(12) United States Patent
Cheng et al.

(10) Patent No.: US 7,056,717 B2
(45) Date of Patent: Jun. 6, 2006

(54) GENES INVOLVED IN ISOPRENOID COMPOUND PRODUCTION

(75) Inventors: Qiong Cheng, Wilmington, DE (US); Mattheos Koffas, Wilmington, DE (US); Kelley C. Norton, Avondale, PA (US); James M. Odom, Kennett Square, PA (US); Stephen K. Picataggio, Landenberg, PA (US); Andreas Schenzle, Zurich (CH); Jean-Francois Tomb, Wilmington, DE (US); Pierre E. Rouviere, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 140 days.

(21) Appl. No.: 10/700,003

(22) Filed: Nov. 3, 2003

(65) Prior Publication Data

US 2004/0063143 A1 Apr. 1, 2004

Related U.S. Application Data

(62) Division of application No. 09/934,903, filed on Aug. 22, 2001, now Pat. No. 6,660,507.

(60) Provisional application No. 60/229,907, filed on Sep. 1, 2000.

(51) Int. Cl.
*C12N 9/12* (2006.01)
*C12N 1/20* (2006.01)
*C12P 23/00* (2006.01)
*C12P 21/04* (2006.01)
*C07H 21/04* (2006.01)

(52) U.S. Cl. .......... 435/194; 435/183; 435/67; 435/252.3; 435/320.1; 435/69.1; 435/71.1; 435/410; 435/415; 435/419; 435/243; 435/253.1; 536/23.2; 536/23.7

(58) Field of Classification Search .......... 435/67, 435/194, 252.3, 320.1, 23.2, 69.1, 41, 71.1, 435/415–419, 440, 410, 243, 253.1; 536/23.2, 536/23.7
See application file for complete search history.

(56) References Cited

U.S. PATENT DOCUMENTS

| | | | |
|---|---|---|---|
| 5,429,939 A | 7/1995 | Misawa et al. | |
| 5,530,189 A | 6/1996 | Ausich et al. | |
| 6,107,058 A | 8/2000 | Gwynn et al. | |

FOREIGN PATENT DOCUMENTS

| | | |
|---|---|---|
| EP | 0747483 A2 | 12/1996 |
| EP | 0816490 A2 | 1/1998 |

(Continued)

OTHER PUBLICATIONS

Sequence Alignment.*

(Continued)

*Primary Examiner*—Manjunath Rao
*Assistant Examiner*—Yong Pak

(57) ABSTRACT

Genes have been isolated from *Methylomonas* 16a sp. encoding the isoprenoid biosynthetic pathway. The genes and gene products are the first isolated from a *Methylomonas* strain that is capable of utilizing single carbon (C1) substrates as energy sources. The genes and gene products of the present invention may be used in a variety of ways for the production of isoprenoid compounds in a variety of organisms.

7 Claims, 4 Drawing Sheets

FOREIGN PATENT DOCUMENTS

| | | |
|---|---|---|
| EP | 0872554 A2 | 10/1998 |
| EP | 0974661 A1 | 12/1998 |
| EP | 0855363 A2 | 11/1999 |
| EP | 1043403 A1 | 10/2000 |
| EP | 1063297 A1 | 12/2000 |
| EP | 1072683 A1 | 1/2001 |
| WO | WO 9723633 A1 | 7/1997 |
| WO | WO 9735966 A1 | 10/1997 |
| WO | WO 9911757 A1 | 3/1999 |
| WO | WO 9958649 A1 | 11/1999 |
| WO | WO 0034448 A1 | 6/2000 |
| WO | WO 0044912 A1 | 8/2000 |
| WO | WO 0046346 A1 | 8/2000 |
| WO | WO 00/61792 A1 | 10/2000 |
| WO | WO 0061793 A2 | 10/2000 |
| WO | WO 0063389 A1 | 10/2000 |
| WO | WO 0065036 A1 | 11/2000 |
| WO | WO 0111055 A1 | 2/2001 |
| WO | WO 01/85950 A2 | 11/2001 |
| WO | WO 0183769 A2 | 11/2001 |
| WO | WO 0194561 A3 | 12/2001 |

OTHER PUBLICATIONS

Newell et al. Plant transformation technology. Developments and applications. Mol Biotechnol. Sep. 2000; 16(1):53-65. Review.*

Spurgeon and Porter, Biosynthesis of Isoprenoid Compounds, pp 3-46, A Wiley-Interscience Publicaiton, 1981.

Horbach et al., Isoprenoid biosynthesis in bacteria: Two Different pathways? FEMS Microbiol. Lett. 111:135-140, 1993.

Rohmer et al., Isoprenoid biosynthesis in bacteria: a novel pathway for the early steps leading to isopentenyl diphosphate, Biochem. 295: 517-524, 1993.

Schwender et al., Biosynthesis of isoprenoids via a novel pyrvate/glyceraldehyde 3-phosphate non-mevalonate pathway in the green alga Scenedesmus obiquus, Biochem., 316, 73-38, 1996.

Eisenreich et al., Studies on the biosynthesis of taxol: The taxane carbon skeleton in not of mevalonoid origin, Proc. Natl. Acad. Sci. USA 93: 6431-6436, 1998.

Lois et al., Cloning and characterization of a gene from *Escherichia coli* encoding a transketolase-like enzyme that catalyzes synthesis of D-1-deoxyxyfulose 5-phosphte, a common precursor for Isoprenoid, thiamin, and pyridoxol biosynthesis, Proc. Natl. Acad. Sci. USA 95: 2105-2110, 1998.

Takahashi et al., A 1-deoxy-D-xylulose 5-phosphate reductoisomerase catalyzing the formulation of 2-C-methyl-D-erythritol 4-phosphate in an alternative nonmevalonate pathway for terpenoid biosynthesis, Proc. Natl. Acad. Sci. USA 95:9879-9884, 1998.

4-diphosphocytidyl-2C-methyl-d-erythritol synthase, SwissProt#Q46893, Nov. 1, 1997.

4-diphosphocytidyl-2-c-methyl-d-erythritol kinase, SwissProt#P24209, Mar. 1, 1992.

Luttgen et al., Biosynthesis of terpenoids: YchB protein of *Escherichia coli* phosphorylates the 2-hydroxy group of 4-diphosphocylidyl-2C-methyl-D-erythritol, Proc. Natl. Acad. Sci. USA 97: 1062-1067, 2000.

Lee et al., Erythroid Kruppel-like factor is recruited to the CACCC box in the β-globin promoter. The role of the neighboring promoter elements, Proc. Natl. Acad. Sci. USA 97: 2468-2490, 2000.

2C-methyl-d-erythritol 2,4-cyclodiphosphate synthase, SwissProt#P36663, Jun. 1, 1994.

Weng et al., Nucleotide Sequence of *Escherichia coli* pyrG Encoding CTP Synthetase, J. Biol. Chem., 261: 5568-5574, 1986.

Lange and Croteau, Isopentenyl diphosphate biosynthesis via a mevalonate-independent pathway. Isopentenyl monophosphate kinase catalyzes the terminal enzymatic step, Proc. Natl. Acad. Sci. USA 96: 13714-13719, 1999.

Cunningham et al., Evidence of Role for LytB in the Nonmevalonate Pathway of Isoprenoid, Biosynthesis, J. of Bacteriol. 182: 5841-5848, 2000.

Rohdich et al., Cytidine 5'-triphosphate-dependent biosynthesis of isoprenolds:, Proc. Natl. Acad. Sci. USA, Oct. 12, 1999; 96(21):11758-63.

Herz et al., Biosynthesis of terpenoids, YgbBprotein converts 4-diphosphocytidyl-2C-methyl-D-erythritol 2-phosphate to 2C-methyl-D-erthritol 2,4-cyclodiphosphate, Proc. Natl. Acad. Sci. USA, Mar. 14, 2000: 97(6):2489-90.

Ohto et al., A thermophilic cyanobacterium Synechococcus elongatus has three different Class 1 prenyltransferases genes, Plant Mol. Biol. 40(2), 307-321, 1999.

Xiong, et al., Tracking molecular evolution of photosynthesis by characterization of a major photosynthesis gene cluster from heliobacillus mobillis, Proc. Natl. Acad. Sci. U.S.A. 95(25), 14851-14856, 1998.

Rodriguez-Concepcion et al., Genetic evidence of branching in the isoprenoid pathway for the production of isopentenyl diphosphate and dimethylallyl diphosphate in *Escherichia coli*, FEBS Letters, vol. 473, No. 3, May 19, 2000, pp. 328-332, XP00218415.

Rohmer, M., Isoprenoid Biosynthesis via, the Mevaionate-Independent Route, A Novel Target for Antibacterial Drugs?, Progress in Drug Research, Basel: Birkhaeuser, CH, vol. 50, 1998, pp. 135-154, XP000906878.

Lois et al., Clining and Characterization of a gene from *Escherichia coli* encoding a transketolase-like enzyme that catalyyzes the synthesis of D-1-deoxyxylulose 5-phosphate, a common precursor for isoprenoid, thiamin, and pyridoxol biosynthesis, FASEB Journal, Fed. Of American Soc. For Experimental Biology, Bethesda, MD, vol. 95, Mar. 1998, pp. 2105-2110.

Scolnik et al., A Table of Some Cloned Plant Genes Involved in Isoprenoid Biosynthesis, Plant Molecular Biology Reporter, New York, NY vol. 14, No. 4, Dec. 1998, pp. 305-319, XP000884796.

Bartley et al., Molecular Biology of Carotenoid Biosynthesis in Plants, Annual Review of Plant Physiology and Plant Molecular Biology, Annual Reviews Inc, vol. 45, 1994, pp. 287-301, XP000881128.

Rohmer, Isoprenoid Biosynthesis via the Mevalonate-Independent Route, A novel Target for Antibacterial Drugs?, Progress in Drug Research, Basel, vol. 50, 1998, pp. 135-154, XP000906878.

Hanson et al., Methanotrophic bacteria, Microbiological Reviews, American Societyfor Microbiology, Washington, D.C., vol. 60, No. 2, Jun. 1996, pp. 439-471.

Zhu Xufen et al., Geranylgeranyl pyrophosphate synthase encoded by the newly isolated gene GGPS6 from Arabidopsis thaliana is localized in mitochondria, Plant Molecular Biology, Nijhoff Publishers, Dordrecht, NL, vol. 35, No. 3, 1997, pp. 331-341, XP002153683.

Misawa et al., "Elucidation of the Erwinia Uredovora Carenoid Biosynthetic Pathway by Functional Analysis fo Gene Products Expressed in *Escherichia Coli*", Journal of Bacteriology, Washington, D.C., vol. 172, No. 12, Dec. 1990, pp. 6704-6712.

Lange and Croteau, Isopentenyl diphosphate biosynthesis via a mevalonate-independent pathway: Isopentenyl monophosphate kinase catalyzes the terminal enzymatic step, Proc. Natl. Acad. Sci. USA 98: 13714-13719, 1999.

Cunningham et al., Evidence of Role for LytB in the Nonmevalonate Pathway of Isoprenoid, Biosynthesis. J. of Bacteriol. 182: 5841-5848, 2000.

Link, C. et al., Acinetobacter sp. BD413 lyB, comb, comG, Come, and comF genes, complete cds: and unknown genes, Sep. 21, 1999, Gen Bank Accession No. AF027189.

Cassler-Chauvat, C., Synechocystis sp. Insertion sequences IS5Sb, IS4Sa and manner-like insertion sequence ISTcSa, LytB gene, complete cds, and putative transposase genes, partial cds, Oct. 17, 1995, Gen Bank Accession No. U38915.

Rohdich et al., Cytidine 5'-triphosphate-dependent biosynthesis of Isoprenolds:, Proc. Natl. Acad. Sci. USA Oct. 12, 1999: 98 (21):11758-63.

Herz et al., Biosynthesis of terpenoids, YgbBprotein converts 4-diphosphocytidyl-2C-methyl-D-erythritol 2-phosphate to 2C-methyl-D-erthritol 2,4-cyclodiphosphate, Proc. Natl. Acad. Sci. USA, Mar. 14, 2000: 97(6):2486-90.

Ohlo et al., A thermophilic cyanobacterium Synechococcus elangatus has three different Class I prenythransferases genes, Plant, Mol. Biol. 40(2), 307-321, 1999.

Xiong, et al., Tracking molecular evolution of photosynthesis by characterization of a major photosynthesis gene cluster from heliobacillus mobilis, Proc. Natl. Acad. Sci. U.S.A. 95(25), 14851-14855, 1998.

Wieland, KP and Goetz, F., S.aureus orfs 1,2,3 & 4., May 17, 1996, Gen Bank Accession No. X97985.

Herzberg, C. et al., LytB [Acinetobacter sp. BD413], Sep. 21, 1999, Gen Bank Accession No. AAD55804.

* cited by examiner

US 7,056,717 B2

GENES INVOLVED IN ISOPRENOID COMPOUND PRODUCTION

This application is a divisional of U.S. patent application Ser. No. 09/934,903, filed on Aug. 22, 2001, now granted as U.S. Pat. No. 6,660,507 and claims the benefit of U.S. Provisional Application No. 60/229,907, filed Sep. 1, 2000.

FIELD OF THE INVENTION

This invention is in the field of microbiology. More specifically, this invention pertains to nucleic acid fragments encoding enzymes useful for microbial production of isoprenoid compounds.

BACKGROUND OF THE INVENTION

Isoprenoids are an extremely large and diverse group of natural products that have a common biosynthetic origin, i.e., a single metabolic precursor, isopentenyl diphosphate (IPP). The group of natural products known as isoprenoids includes all substances that are derived biosynthetically from the 5-carbon compound isopentenyl diphosphate. Isoprenoid compounds are also referred to as "terpenes" or "terpenoids", which is the term used in the designation of the various classes of these examples (Spurgeon and Porter, Biosynthesis of Isoprenoid Compounds, pp 3–46, A Wiley-Interscience Publication (1981)).

Isoprenoids are ubiquitous compounds found in all living organisms. Some of the well-known examples of isoprenoids are steroids (triterpenes), carotenoids (tetraterpenes), and squalene, just to name a few.

For many years, it was accepted that IPP was synthesized through the well-known acetate/mevalonate pathway. However, recent studies have demonstrated that the mevalonate-dependent pathway does not operate in all living organisms. An alternate mevalonate-independent pathway for IPP biosynthesis was initially characterized in bacteria and later also in green algae and higher plants (Horbach et al., *FEMS Microbiol. Lett.* 111:135–140 (1993); Rohmer et al, *Biochem.* 295: 517–524 (1993); Schwender et al., *Biochem.* 316: 73–80 (1996); Eisenreich et al., *Proc. Natl. Acad. Sci. USA* 93: 6431–6436 (1996)).

Many steps in both the mevalonate-independent and mevalonate-dependent isoprenoid pathways are known. For example, the initial steps of the alternate pathway involve the condensation of 3-carbon molecules (pyruvate and C1 aldehyde group, D-glyceraldehyde 3-phosphate), to yield the 5-carbon compound D-1-deoxyxylulose-5-phosphate. Lois et al. has reported a gene, dxs, that encodes D-1-deoxyxylulose-5-phosphate synthase (DXS) and that catalyzes the synthesis of D-1-deoxyxylulose-5-phosphate in *E. coli* (*Proc. Natl. Acad. Sci. USA* 95: 2105–2110 (1998)).

Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR). Takahashi et al. reported that the dxr gene product catalyzes the formation of 2-C-methyl-D-erythritol-4-phosphate in the alternate pathway in *E. coli* (*Proc. Natl. Acad. Sci. USA* 95: 9879–9884 (1998)).

Steps converting 2-C-methyl-D-erythritol-4-phosphate to isopentenyl monophosphate are not well characterized, although some steps are known. 2-C-methyl-D-erythritol-4-phosphate is converted into 4-diphosphocytidyl-2C-methyl-D-erythritol in a CTP dependent reaction by the enzyme encoded by non-annotated gene ygbP. Rohdich et al. reported that the YgbP protein in *E. coli* catalyzes the reaction mentioned above. Recently, ygbP gene was renamed as ispD as a part of the isp gene cluster (SwissProt #Q46893) (*Proc. Natl. Acad. Sci. USA* 96:11758–11763 (1999)).

Then the 2 position hydroxy group of 4-diphosphocytidyl-2C-methyl-D-erythritol can be phosphorylated in an ATP dependent reaction by the enzyme encoded by the ychB gene. Luttgen et al. has reported that the YchB protein in *E. coli* phosphorylates 4-diphosphocytidyl-2C-methyl-D-erythritol, resulting in 4-diphosphocytidyl-2C-methyl-D-erythritol 2-phosphate. Recently, the ychB gene was renamed as ispE as a part of the isp gene cluster (SwissProt#P24209) (Luttgen et al., *Proc. Natl. Acad. Sci. USA* 97:1062–1067 (2000)).

Herz et al. reported that the ygbB gene product in *E. coli* converts 4-diphosphocytidyl-2C-methyl-D-erythritol 2-phosphate to 2C-methyl-D-erythritol 2,4-cyclodiphosphate. 2C-methyl-D-erythritol 2,4-cyclodiphosphate can be further converted into carotenoids through the carotenoid biosynthesis pathway (*Proc. Natl. Acad. Sci. USA* 97:2486–2490 (2000)). Recently, the ygbB gene was renamed as ispF as a part of the isp gene cluster (SwissProt #P36663).

The reaction catalyzed by the YgbP enzyme is carried out in a CTP dependent manner. Thus, CTP synthase plays an important role in the isoprenoid pathway. PyrG encoded by the pyrG gene in *E. coli* was determined to encode CTP synthase (Weng et al., *J. Biol. Chem.*, 261:5568–5574 (1986)).

Following several reactions not yet characterized, isopentenyl monophosphate is formed. Isopentenyl monophosphate is converted to isopentenyl diphosphate (IPP) by isopentenyl monophosphate kinase, encoded by the ipk gene, and that is identical to the above mentioned yhcB (ispE) gene (Lange and Croteau, *Proc. Natl. Acad. Sci. USA* 96:13714–13719 (1999)).

Cunningham et al. (*J of Bacteriol.* 182:5841–5848, (2000)) has reported that the lytB gene in *E. coli* that is thought to encode an enzyme of the deoxyxylulose-5-phosphate pathway that catalyzes a step at or subsequent to the point at which the pathway branches to form IPP and dimethylallyl diphosphate. LytB gene is also found in other microorganisms such as *Acinetbacter* and *Synechocystis*, (GenBank Accession Numbers AF027189 and U38915, respectively).

Prenyltransferases constitute a broad group of enzymes catalyzing the consecutive condensation of isopentenyl diphosphate (IPP) resulting in the formation of prenyl diphosphates of various chain lengths. Homologous genes of prenyl transferase have highly conserved regions in their amino acid sequences. Ohto et al. reported three prenyl transferase genes in cyanobacterium *Synechococcus elongatus* (*Plant Mol. Biol.* 40:307–321 (1999)). They are geranylgeranyl (C20) diphosphate synthase, farnesyl (C15) diphosphate synthase and another prenyltransferase that can catalyze the synthesis of five prenyl diphosphates of various lengths.

Further down in the isoprenoid biosynthesis pathway, more genes are involved in the synthesis of specific isoprenoids. As an example, the crtN gene was found in *Heliobacillus mobilis* (Xiang et al., *Proc. Natl. Acad. Sci. USA* 95:14851–14856 (1998)) to encode diapophytoene dehydrogenase is a part of the carotenoid biosynthesis pathway.

Although most of the genes involved in the isoprenoid pathways are known, the genes involved in the isoprenoid pathway of methanotrophic bacteria are not described in the existing literature. However, there are many pigmented methylotrophic and methanotrophic bacteria, which suggests that the ability to produce carotenoid pigments is widespread in these bacteria and therefore the genes must be widespread in these bacteria. Applicants have isolated a number of unique open reading frames encoding enzymes of the isoprenoid biosynthesis pathway from a *Methylomonas* sp.

Applicants have solved the stated problem by isolating genes containing 9 open reading frames (ORFs) encoding enzymes involved in isoprenoid synthesis.

SUMMARY OF THE INVENTION

The present invention provides an isolated nucleic acid molecule encoding a isoprenoid biosynthetic enzyme, selected from the group consisting of: (a) an isolated nucleic acid molecule encoding the amino acid sequence selected from the group consisting of SEQ ID NOs:2, 4, 6, 8, 10, 12, 14, 16, 18 and 24; (b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and (c) an isolated nucleic acid molecule that is complementary to (a) or (b).

Additionally the invention provides polypeptides encoded by the present genes and chimera where the genes are under the control of suitable regulatory sequences. Similarly the invention provides transformed organisms, including bacteria, yeast, filamentous fungi, and green plants expressing one or more of the present genes and gene products.

The present invention provides methods of obtaining all or substantial portions of the instant genes through gene amplification or hybridization methods.

In another embodiment the invention provides methods for the production of isoprenoids comprising: contacting a transformed host cell under suitable growth conditions with an effective amount of a carbon source whereby an isoprenoid compound is produced, said transformed host cell comprising a set of nucleic acid molecules encoding SEQ ID NOs:2, 4, 6, 8, 10, 12, 14, 16, 18, and 24 under the control of suitable regulatory sequences.

Similarly the invention provides a method of regulating isoprenoid biosynthesis in an organism comprising, overexpressing at least one isoprenoid gene selected from the group consisting of SEQ ID NO:1, 3, 5, 7, 9, 11, 13, 15, 17 and 23 in an organism such that the isoprenoid biosynthesis is altered in the organism.

In another embodiment the invention provides a mutated gene encoding a isoprenoid enzyme having an altered biological activity produced by a method comprising the steps of (i) digesting a mixture of nucleotide sequences with restriction endonucleases wherein said mixture comprises:
 a) a native isoprenoid gene;
 b) a first population of nucleotide fragments which will hybridize to said native isoprenoid gene;
 c) a second population of nucleotide fragments which will not hybridize to said native isoprenoid gene;

wherein a mixture of restriction fragments are produced; (ii) denaturing said mixture of restriction fragments; (iii) incubating the denatured said mixture of restriction fragments of step (ii) with a polymerase; (iv) repeating steps (ii) and (iii) wherein a mutated isoprenoid gene is produced encoding a protein having an altered biological activity.

BRIEF DESCRIPTION OF THE DRAWINGS, SEQUENCE DESCRIPTIONS, AND THE BIOLOGICAL DEPOSITS

Figure 3A:
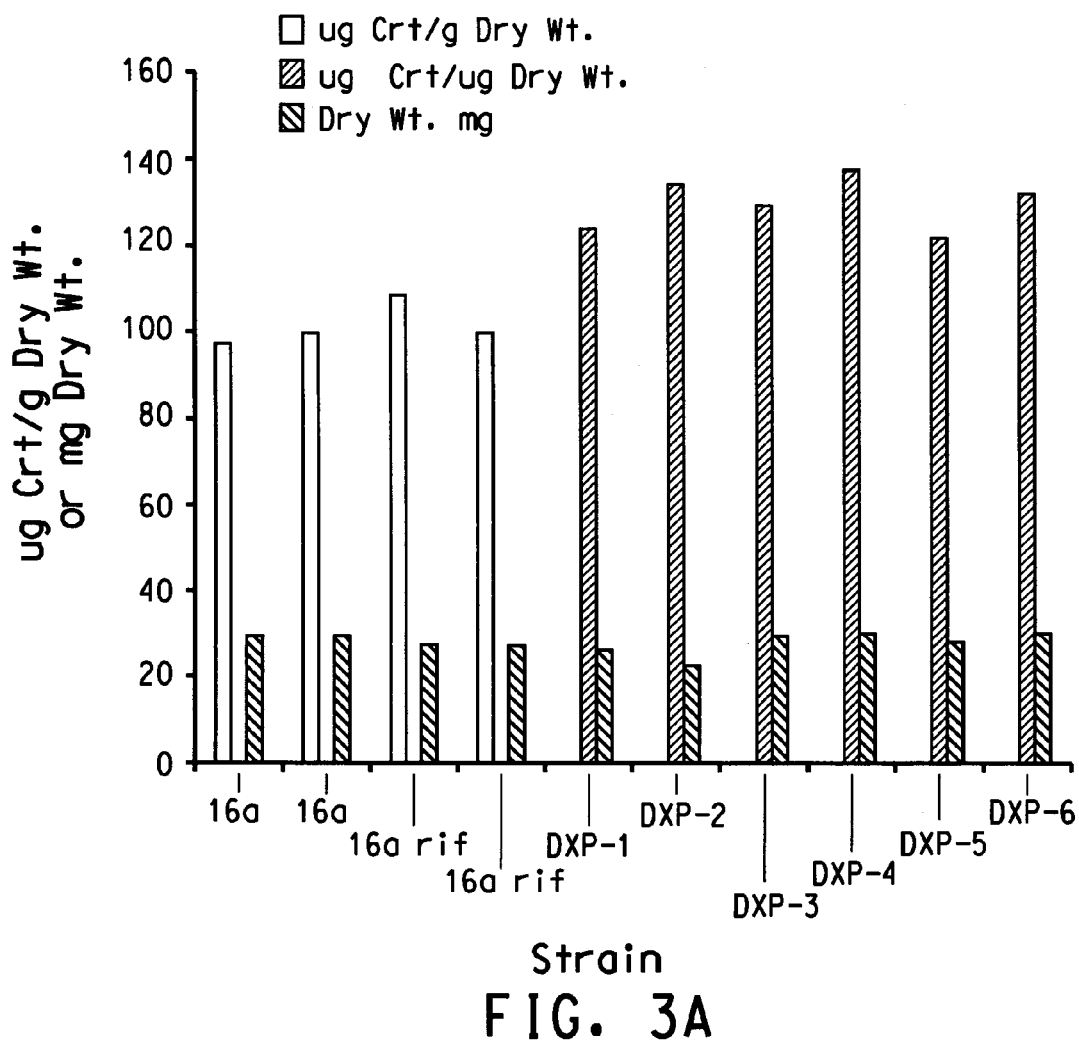
Figure 3B:
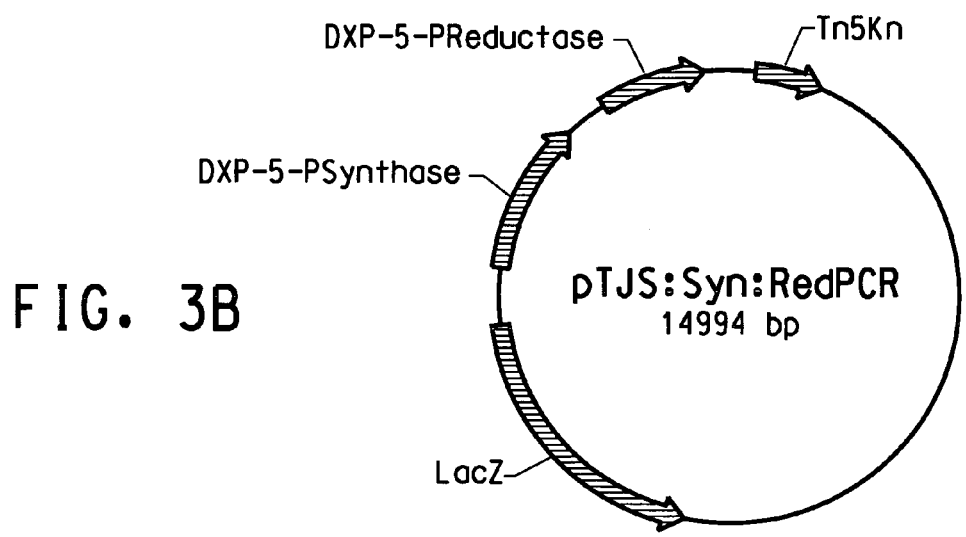

FIG. 3a shows a gene dose effect on carotenoid biosynthesis. Two cultures of the native strain of *Methylomonas* 16a, designated as 16a, and two cultures of a rif-resistant variant of the native strain, designated as 16a-rif (without plasmid), served as negative controls. Six isolated transconjugants were labeled as DXP-1 through DPX-6. FIG. 3b shows the plasmid that contains the dxs and dxr genes.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of ORF 1 encoding the dxs gene.

SEQ ID NO:2 is the deduced amino acid sequence of dxs encoded by ORF 1.

SEQ ID NO:3 is the nucleotide sequence of ORF 2 encoding the dxr gene.

SEQ ID NO:4 is the deduced amino acid sequence of dxr encoded by ORF 2.

SEQ ID NO:5 is the nucleotide sequence of ORF 3 encoding the ygbP (ispD) gene.

SEQ ID NO:6 is the deduced amino acid sequence of ygbP (ispD) gene encoded by ORF 3.

SEQ ID NO:7 is the nucleotide sequence of ORF 4 encoding the ychB (ispE) gene.

SEQ ID NO:8 is the deduced amino acid sequence of ychB (ispE) encoded by ORF 4.

SEQ ID NO:9 is the nucleotide sequence of ORF 5 encoding the ygbB (ispF) gene.

SEQ ID NO:10 is the deduced amino acid sequence of ygbB (ispF) encoded by ORF 5.

SEQ ID NO:11 is the nucleotide sequence of ORF 6 encoding the pyrG gene.

SEQ ID NO:12 is the deduced amino acid sequence of pyrG encoded by ORF 6.

SEQ ID NO:13 is the nucleotide sequence of ORF 7 encoding the ispA gene.

SEQ ID NO:14 is the deduced amino acid sequence of ispA gene encoded by ORF 7.

SEQ ID NO:15 is the nucleotide sequence of ORF 8 encoding the crtN gene, copy1.

SEQ ID NO:16 is the deduced amino acid sequence of crtN gene copy1 encoded by ORF 8.

SEQ ID NO:17 is the nucleotide sequence of ORF 9 encoding the crtN gene copy2.

SEQ ID NO:18 is the deduced amino acid sequence of crtN gene copy2 encoded by ORF 9.

SEQ ID NO:19 and 20 are the primer sequences used to amplify the dxs gene.

SEQ ID NO:21 and 22 are the primer sequences used to amplify the dxr gene.

SEQ ID NO:23 is the nucleotide sequence of ORF 10 encoding the IytB gene.

SEQ ID NO:24 is the deduced amino acid sequence of the IytB gene encoded by ORF 10.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
| --- | --- | --- |
| Methylomonas 16a | ATCC PTA 2402 | Aug. 21, 2000 |

DETAILED DESCRIPTION OF THE INVENTION

The genes and their expression products are useful for the creation of recombinant organisms that have the ability to produce various isoprenoid compounds. Nucleic acid fragments encoding the above mentioned enzymes have been isolated from a strain of *Methylomonas* 16a and identified by comparison to public databases containing nucleotide and protein sequences using the BLAST and FASTA algorithms well known to those skilled in the art.

The genes and gene products of the present invention may be used in a variety of ways for the enhancement or manipulation of isoprenoid compounds.

The microbial isoprenoid pathway is naturally a multiproduct platform for production of compounds such as carotenoids, quinones, squalene, and vitamins. These natural products may be from 5 carbon units to more than 55 carbon units in chain length. There is a general practical utility for microbial isoprenoid production for carotenoid compounds as these compounds are very difficult to make chemically (Nelis and Leenheer, *Appl. Bacteriol.* 70:181–191 (1991)). Most carotenoids have strong color and can be viewed as natural pigments or colorants. Furthermore, many carotenoids have potent antioxidant properties and thus inclusion of these compounds in the diet is thought to healthful. Well-known examples are β-carotene and astaxanthin.

In the case of *Methylomonas* 16a, the inherent capacity to produce carotenoids is particularly useful. This is because methanotrophic bacteria have been used for the commercial production of single cell protein and the protein from these bacteria is known to be efficacious as animal feeds (Green, Taxonomy of Methylotrophic Bacteria. In: Methane and Methanol Utilizers (Biotechnology Handbooks 5) J. Colin Murrell and Howard Dalton eds. 1992 Pleanum Press NY. Pp 23–84; BioProtein Manufacture 1989. Ellis Horwood series in applied science and industrial technology. NY: Halstead Press.)

The genes and gene sequences described herein enable one to incorporate the production of healthful carotenoids directly into the single cell protein product derived from *Methylomonas* 16a. This aspect makes this strain or any methanotrophic strain into which these genes are incorporated a more desirable production host for animal feed due to the presence of carotenoids which are known to add desirable pigmentation and health benefits to the feed. Salmon and shrimp aquacultures are particularly useful applications for this invention as carotenoid pigmentation is critically important for the value of these organisms. (F. Shahidi, J. A. Brown, Carotenoid pigments in seafood and aquaculture Critical reviews in food Science 38(1): 1–67 (1998)).

In addition to feed additives, the genes are useful for the production of carotenoids and their derivatives, isoprenoid intermediates and their derivatives, and as pure products useful as pigments, flavors and fragrances.

In this disclosure, a number of terms and abbreviations are used.

The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "isoprenoid" or "terpenoid" refers to any molecule derived from the isoprenoid pathway including 10-carbon terpenoids and their derivatives, such as carotenoids and xanthophylls.

The term "*Methylomonas* 16a" and "*Methylomonas* 16a sp." are used interchangeably and refer to the *Methylomonas* strain used in the present invention.

The term "Dxs" refers to the 1-deoxyxylulose-5-phosphate synthase enzyme encoded by the dxs gene represented in OFR1.

The term "Dxr" refers to the 1-deoxyxylulose-5-phosphate reductoisomerase enzyme encoded by the dxr gene represented in ORF 2.

The term "YgbP" or "IspD" refers to the 2C-methyl-D-erythritol cytidyltransferase enzyme encoded by the ygbP or ispD gene represented in ORF 3. The names of the gene, ygbP or ispD, are used interchangeably in this application. The names of gene product, YgbP or IspD are used interchangeably in this application.

The term "YchB" or "IspE" refers to 4-diphosphocytidyl-2-C-methylerythritol kinase enzyme encoded by ychB or ispE gene represented in ORF 4. The names of the gene, ychB or ispE, are used interchangeably in this application. The names of gene product, YchB or IspE are used interchangeably in this application.

The term "YgbB" or "IspF" refers to the 2C-methyl-d-erythritol 2,4-cyclodiphosphate synthase enzyme encoded by the ygbB or ispF gene represented in ORF 5. The names of the gene, ygbB or ispF, are used interchangeably in this application. The names of gene product, YgbB or IspF are used interchangeably in this application.

The term "PyrG" refers to the CTP synthase enzyme encoded by the pyrG gene represented in ORF 6.

The term "IspA" refers to the geranyltransferase or farnesyl diphosphate synthase enzyme, as one of the prenyl transferase family encoded by the ispA gene represented in ORF 7.

The term "CrtN1" or "CrtN, copy1" refers to copy 1 of the diapophytoene dehydrogenase enzyme encoded by the crtN1 gene represented in ORF 8.

The term "CrtN2" or "CrtN copy2" refers to copy 2 of the diapophytoene dehydrogenase enzyme encoded by the crtN2 gene represented in ORF 9.

The term "LytB" refers to the protein encoded by the lytB gene represented in ORF 10, functioning in the formation of IPP and dimethylallyl diphosphate in the isoprenoid pathway.

The term "Embden-Meyerhof pathway" refers to the series of biochemical reactions for conversion of hexoses such as glucose and fructose to important cellular 3-carbon intermediates such as glyceraldehyde 3 phosphate, dihydroxyacetone phosphate, phosphoenol pyruvate and pyruvate. These reactions typically proceed with net yield of biochemically useful energy in the form of ATP. The key enzymes unique to the Embden-Meyerof pathway are the phosphofructokinase and fructose 1,6 bisphosphate aldolase.

The term "Entner-Douderoff pathway" refers to a series of biochemical reactions for conversion of hexoses such as glucose or fructose to the important 3 carbon cellular intermediates pyruvate and glyceraldehyde 3 phosphate without any net production of biochemically useful energy. The key enzymes unique to the Entner-Douderoff pathway are the 6 phosphogluconate dehydratase and a ketodeoxyphosphogluconate aldolase.

The term "high growth methanotrophic bacterial strain" refers to a bacterium capable of growth with methane or methanol as the sole carbon and energy source and which possess a functional Embden-Meyerof carbon flux pathway resulting in a high rate of growth and yield of cell mass per gram of C1 substrate metabolized. The specific "high growth methanotrophic bacterial strain" described herein is referred to as "*Methylomonas* 16a" or "16a", which terms are used interchangeably.

The term "methanotroph" or "methanotrophic bacteria" will refer to a prokaryotic microorganism capable of utilizing methane as its primary carbon and energy source.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Sequence Identification

Figure 1A:
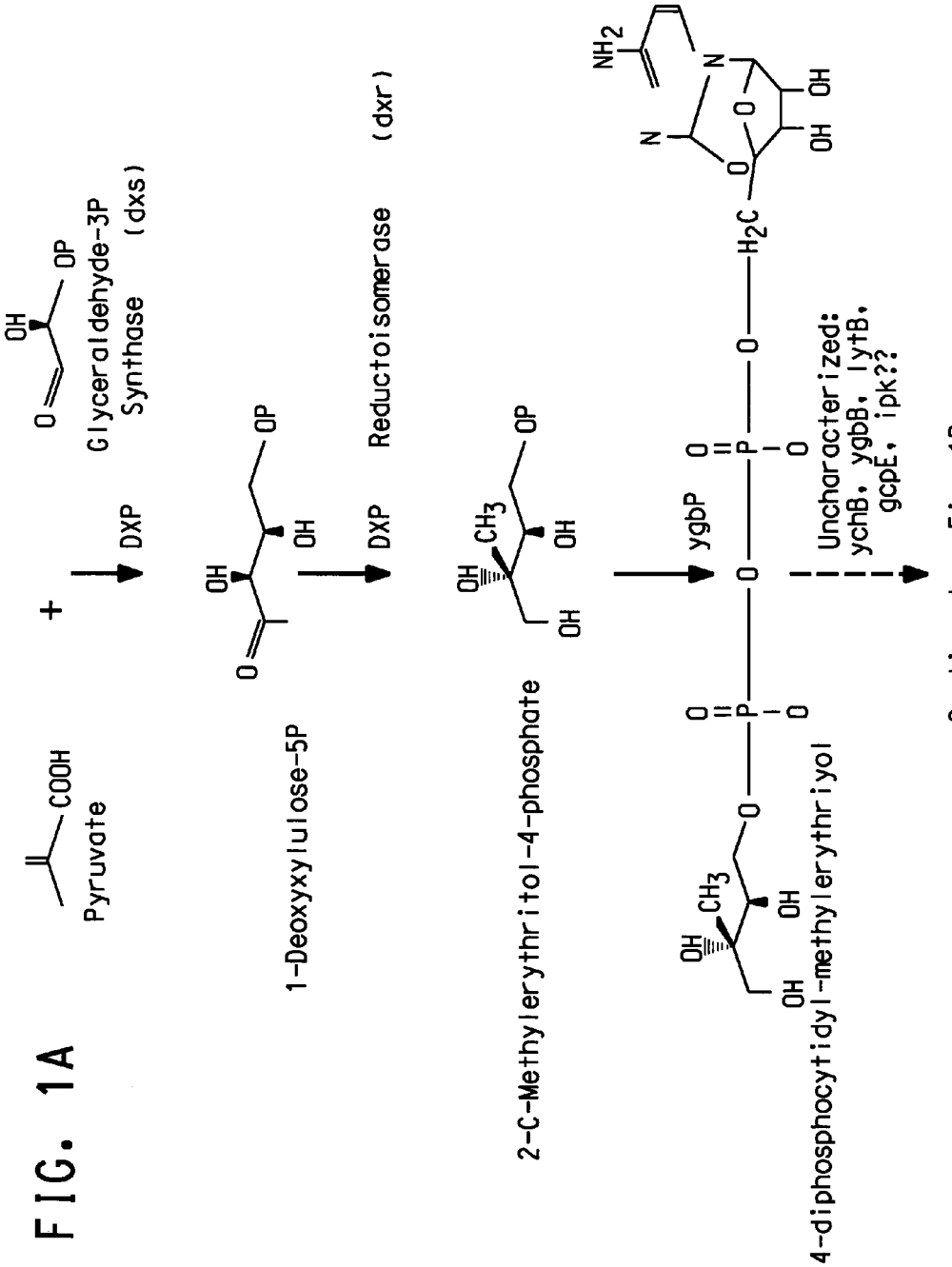
FIG. 1 shows the isoprenoid pathway.
Figure 1B:
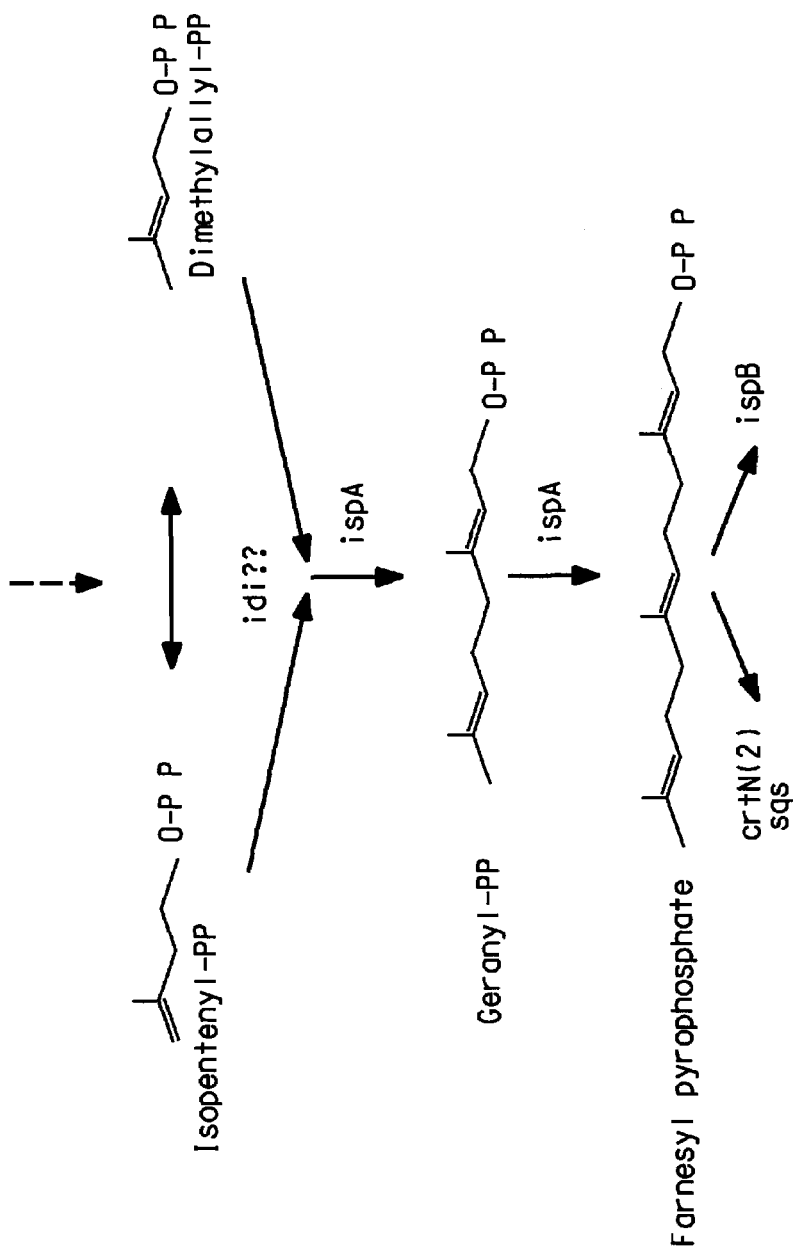

A variety of nucleotide sequences have been isolated from *Methylomonas* 16a encoding gene products involved in the isoprenoid production pathway. ORF's 1–6 for example encode enzymes early in the isoprenoid pathway (FIG. 1) leading to IPP, which is the precursor of all isoprenoid compounds. ORF 7 encodes the IspA enzyme that is involved in elongation by condensing IPP precursors. ORF 8 and ORF 9 are involved more specifically in carotenoid production.

Comparison of the dxs nucleotide base and deduced amino acid sequences (ORF 1) to public databases reveals that the most similar known sequences range from about 60% identical to the amino acid sequence of reported herein over length of 620 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). More preferred amino acid fragments are at least about 80%–90% identical to the sequences herein. Most preferred are nucleic acid fragments that are at least 95% identical to the amino acid fragments reported herein. Similarly, preferred Dxs encoding nucleic acid sequences corresponding to the instant ORF's are those encoding active proteins and which are at least 80% identical to the nucleic acid sequences of reported herein. More preferred Dxs nucleic acid fragments are at least 90% identical to the sequences herein. Most preferred are Dxs nucleic acid fragments that are at least 95% identical to the nucleic acid fragments reported herein.

Comparison of the Dxr base and deduced amino acid sequence to public databases reveals that the most similar known sequence is 55% identical at the amino acid level over a length of 394 amino acids (ORF 2) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred Dxr encoding nucleic acid sequences corresponding to the instant ORF are those encoding active proteins and which are at least 80% identical to the nucleic acid sequences of reported herein. More preferred Dxr nucleic acid fragments are at least 90% identical to the sequences herein. Most preferred are Dxr nucleic acid fragments that are at least 95% identical to the nucleic acid fragments reported herein.

Comparison of the YgbP (IspD) base and deduced amino acid sequences to public databases reveals that the most similar known sequences range from about 52% identical at the amino acid level over a length of 231 amino acids (ORF 3) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred YgbP (IspD) encoding nucleic acid sequences corresponding to the instant ORF are those encoding active proteins and which are at least 80% identical to the nucleic acid sequences of reported herein. More preferred YgbP (IspD) nucleic acid fragments are at least 90% identical to the sequences herein. Most preferred are YgbP (IspD) nucleic acid fragments that are at least 95% identical to the nucleic acid fragments reported herein.

Comparison of the YchB (IspE) base and deduced amino acid sequences to public databases reveals that the most similar known sequences range from about 50% identical at the amino acid level over a length of 285 amino acids (ORF 4) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred YchB (IspE) encoding nucleic acid sequences corresponding to the instant ORF are those encoding active proteins and which are at least 80% identical to the nucleic acid sequences of reported herein. More preferred YchB (IspE) nucleic acid fragments are at least 90% identical to the sequences herein. Most preferred are YchB (IspE) nucleic acid fragments that are at least 95% identical to the nucleic acid fragments reported herein.

Comparison of the YgbB (IspF) base and deduced amino acid sequences to public databases reveals that the most similar known sequences range from about 69% identical at the amino acid level over a length of 157 amino acids (ORF 5) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred YgbB (IspF) encoding nucleic acid sequences corresponding to the instant ORF are those encoding active proteins and which are at least 80% identical to the nucleic acid sequences of reported herein. More preferred YgbB (IspF) nucleic acid fragments are at least 90% identical to the sequences herein. Most preferred are YgbB (IspF) nucleic acid fragments that are at least 95% identical to the nucleic acid fragments reported herein.

Comparison of the PyrG base and deduced amino acid sequences to public databases reveals that the most similar known sequences range from about 67% identical at the amino acid level over a length of 544 amino acids (ORF 6) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred PyrG encoding nucleic acid sequences corresponding to the instant ORF are those encoding active proteins and which are at least 80% identical to the nucleic acid sequences of reported herein. More preferred PyrG nucleic acid fragments are at least 90% identical to the sequences herein. Most preferred are PyrG nucleic acid fragments that are at least 95% identical to the nucleic acid fragments reported herein.

Comparison of the IspA base and deduced amino acid sequences to public databases reveals that the most similar known sequences range from about 57% identical at the amino acid level over a length of 297 amino acids (ORF 7) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred IspA encoding nucleic acid sequences corresponding to the instant ORF are those encoding active proteins and which are at least 80% identical to the nucleic acid sequences of reported herein. More preferred IspA nucleic acid fragments are at least 90% identical to the sequences herein. Most preferred are IspA nucleic acid fragments that are at least 95% identical to the nucleic acid fragments reported herein.

Comparison of the copy 1 of CrtN base and deduced amino acid sequences to public databases reveals that the most similar known sequences range from about 34% identical at the amino acid level over a length of 511 amino acids (ORF 8) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred nucleic acid sequences corresponding to the instant ORF are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

Comparison of the copy 2 of CrtN base and deduced amino acid sequences to public databases reveals that the most similar known sequences range from about 34% identical at the amino acid level over a length of 497 amino acids (ORF 9) using a Smith-Waterman alignment algorithm (W. R. Pearson supra). More preferred amino acid fragments are at least about 80%–90% identical to the sequences herein. Most preferred are nucleic acid fragments that are at least 95% identical to the amino acid fragments reported herein. Similarly, preferred nucleic acid sequences corresponding to the instant ORF are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

Comparison of the LytB base and deduced amino acid sequences to public databases reveals that the most similar known sequences range from a about 65% identical at the amino acid level over a length of 318 amino acids (ORF 10) using a Smith-Waterman alignment algorithm (W. R. Pearson supra). It has been reported that expression of IytB gene in *E. coli* significantly enhanced accumulation of carotenoids when the *E. coli* was engineered to express carotenoid (Cunningham et al., *J of Bacteriol.* 182:5841–5848 (2000)). More preferred amino acid fragments are at least about 80%–90% identical to the sequences herein. Most preferred are nucleic acid fragments that are at least 95% identical to the amino acid fragments reported herein. Similarly, preferred nucleic acid sequences corresponding to the instant ORF are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

Isolation of Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci. USA* 82, 1074, (1985)) or strand displacement amplification (SDA, Walker, et al., *Proc. Natl. Acad. Sci. U.S.A.,* 89, 392, (1992)).

For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis).

Recombinant Expresion—Microbial

The genes and gene products of the instant sequences may be produced in heterologous host cells, particularly in the cells of microbial hosts. Expression in recombinant microbial hosts may be useful for the expression of various pathway intermediates, or for the modulation of pathways already existing in the host for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include but are not limited to fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Methylococcus, Methylosinus, Methylomicrobium, Methylocystis, Alcaligenes, Synechocystis, Anabaena, Thiobacillus, Methanobacterium* and *Klebsiella*.

Of particular interest in the present invention are high growth obligate methanotrophs having an energetically favorable carbon flux pathway. For example Applicants have discovered a specific strain of methanotroph having several pathway features which make it particularly useful for carbon flux manipulation. This type of strain has served as the host in the present application and is known as *Methylomonas* 16a (ATCC PTA 2402).

The present strain contains several anomalies in the carbon utilization pathway. For example, based on genome sequence data, the strain is shown to contain genes for two pathways of hexose metabolism. The Entner-Douderoff Pathway which utilizes the keto-deoxy phosphogluconate aldolase enzyme is present in the strain. It is generally well accepted that this is the operative pathway in obligate methanotrophs. Also present, however, is the Embden-Meyerhof Pathway, which utilizes the fructose bisphosphate aldolase enzyme. It is well known that this pathway is either not present or not operative in obligate methanotrophs. Energetically, the latter pathway is most favorable and allows greater yield of biologically useful energy, ultimately resulting in greater yield production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes, the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate dependent instead of ATP dependent. This feature adds to the energy yield of the pathway by using pyrophosphate instead of ATP. Because of its significance in providing an energetic advantage to the strain, this gene in the carbon flux pathway is considered diagnostic for the present strain.

In methanotrophic bacteria methane is converted to biomolecules via a cyclic set of reactions known as the ribulose monophosphate pathway or RuMP cycle. This pathway is comprised of three phases, each phase being a series of enzymatic steps. The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by hexulose monophosphate synthase. The second phase is termed "cleavage" and results in splitting of that hexose into two 3-carbon molecules. One of those 3-carbon molecules is recycled back through the RuMP pathway and the other 3-carbon fragment is utilized for cell growth. In methanotrophs and methylotrophs the RuMP pathway may occur as one of three variants. However only two of these variants are commonly found: the FBP/TA (fructose bisphosphotase/Transaldolase) or the KDPG/TA (keto deoxy phosphogluconate/transaldolase) pathway (Dijkhuizen L., G. E. Devries. The Physiology and biochemistry of aerobic methanol-utilizing gram negative and gram positive bacteria. In: Methane and Methanol Utilizers 1992, ed Colin Murrell and Howard Dalton Plenum Press NY).

The present strain is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected whereas the former is not. The finding of the FBP genes in an obligate methane utilizing bacterium is both surprising and suggestive of utility. The FBP pathway is energetically favorable to the host microorganism due to the fact that more energy (ATP) is utilized than is utilized in the KDPG pathway. Thus organisms that utilize the FBP pathway may have an energetic advantage and growth advantage over those that utilize the KDPG pathway. This advantage may also be useful for energy-requiring production pathways in the strain. By using this pathway a methane-utilizing bacterium may have an advantage over other methane utilizing organisms as production platforms for either single cell protein or for any other product derived from the flow of carbon through the RuMP pathway.

Accordingly the present invention provides a method for the production of an isopreoid compound in a high growth, energetically favorable *Methylomonas* strain which
  (a) grows on a C1 carbon substrate selected from the group consisting of methane and methanol; and
  (b) comprises a functional Embden-Meyerhof carbon pathway, said pathway comprising a gene encoding a pyrophosphate dependent phosphofructokinase enzyme.

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes Accordingly it is expected, for example, that introduction of chimeric genes encoding the instant bacterial enzymes under the control of the appropriate promoters, will demonstrate increased isoprenoid production. It is contemplated that it will be useful to express the instant genes both in natural host cells as well as heterologous host. Introduction of the present genes into native host will result in elevated levels of existing isoprenoid production. Additionally, the instant genes may also be introduced into non-native host bacteria where there are advantages to manipulate the isoprenoid compound production that are not present in Methanotrophs.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Pathway Engineering

Knowledge of the sequence of the present genes will be useful in manipulating the isoprenoid biosynthetic pathways in any organism having such a pathway and particularly in methanotrophs. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565, 350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldener et al. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Within the context of the present invention it may be useful to modulate the expression of the identified isoprenoid pathway by any one of the above described methods. For example, the present invention provides a number of genes encoding key enzymes in the terpenoid pathway leading to the production of pigments and smaller isoprenoid compounds. The isolated genes include the dxs and dsr genes, the ispA, D, E, F, and G genes, the pyrG gene and the crtN genes. In particular it may be useful to up-regulate the initial condensation of 3-carbon compounds (pyruvate and C1 aldehyde group, D-glyceraldehyde 3-Phosphate), to yield the 5-carbon compound D-1-deoxyxylulose-5-phosphate mediated by the dxs gene. Alternatively, if it is desired to produce a specific non-pigmented isoprenoid, it may be desirable to disrupt various genes at the downstream end of the pathway. For example, the crtN gene is known to encode diapophytoene dehydrogenase, which is a part of the carotenoid biosynthesis pathway. It may be desirable to use gene disruption or antisense inhibition of this gene if a smaller, upstream terpenoid is the desired product of the pathway.

Industrial Production

Where commercial production of the instant proteins are desired a variety of culture methodologies may be applied. For example, large-scale production of a specific gene product, overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of the instant proteins may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Recombinant Expression—Plants

Plants and algae are also known to produce isoprenoid compounds. The nucleic acid fragments of the instant invention may be used to create transgenic plants having the ability to express the microbial protein. Preferred plant hosts will be any variety that will support a high production level of the instant proteins. Suitable green plants will included but are not limited to soybean, rapeseed (*Brassica napus*, *B.* campestris), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa, L*), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina* and *Dunalliela*. Overexpression of the isoprenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.*, 618 (1–2) (1993)133–145), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100: 1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotides may be used to produce gene products having enhanced or altered activity. Various methods are known for mutating a native gene sequence to produce a gene product with altered or enhanced activity including but not limited to error prone PCR (Melnikov et al., *Nucleic Acids Research,* (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Manatis supra).

Furthermore, a hybrid protein can be assembled by fusion of functional domains using the gene shuffling (exon shuffling) method (Nixon et al., PNAS, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

Gene Expression Profiling

All or portion of the nucleic acid fragments of the instant invention may also be used as probes for gene expression monitoring and gene expression profiling. Many external changes such as changes in growth condition, exposure to chemicals, can cause induction or repression of genes in the cell. The induction or repression of gene can be used for a screening system to determine the best production condition for production organism. On the other hand, by amplifying or disrupting genes, one can manipulate the production of the amount of cellular products as well as the timeline. The genes may be monitored for expression and or regulation of expression by oxygen. It may be desirable to deregulate or derepress these genes by knocking out regulatory elements or over-expressing regulatory elements in order to get the desired product or desired yield.

For example, all or a portion of the instant nucleic acid fragments may be immobilized on a nylon membrane or a glass slide. A Generation II DNA spotter (Molecular Dynamics) is one of the available technology to array the DNA samples onto the coated glass slides. Other array methods are also available and well known in the art. After the cells were grown in various growth conditions or treated with potential candidates, cellular RNA is purified. Fluorescent or radioactive labeled target cDNA can be made by reverse transcription of mRNA. The target mixture is hybridized to the probes, washed using conditions well known in the art. The amount of the target gene expression is quantified by the intensity of radioactivity or fluorescence label (e.g., confocal laser microscope: Molecular Dynamics). The intensities of radioactivity or fluorescent label at the immobilized probes are measured using the technology well known in the art. The two color fluorescence detection scheme (e.g., Cy3 and Cy5) has the advantage over radioactively labeled targets of allowing rapid and simultaneous differential expression analysis of independent samples. In addition, the use of ratio measurements compensates for probe to probe variation of intensity due to DNA concentration and hybridization efficiency. In the case of fluorescence labeling, the two fluorescent images obtained with the appropriate excitation and emission filters constitute the raw data from differential gene expression ratio values are calculated. The intensity of images are analyzed using the available software (e.g., Array Vision 4.0: Imaging Research Inc.) well known in the art and normalized to compensate for the differential efficiencies of labeling and detection of the label. There are many different ways known in the art to normalize the signals. One of the ways to normalize the signal is by correcting the signal against internal controls. Another way is to run a separate array with labeled genomic driven DNA and compare the signal with mRNA driven signals. This method also allows to measure the transcript abundance. The array data of individual gene is examined and evaluated to determine the induction or repression of the gene under the test condition.

DESCRIPTION OF THE PREFERRED EMBODIMENTS

The original environmental sample containing *Methylomonas* 16a was obtained from pond sediment. The pond sediment was inoculated directly into a defined mineral medium under 25% methane in air. Methane was used as the sole source of carbon and energy. Growth was followed until the optical density at 660 nm was stable whereupon the culture was transferred to fresh medium such that a 1:100 dilution was achieved. After 3 successive transfers with methane as the sole carbon and energy source, the culture was plated onto defined minimal medium agar and incubated under 25% methane in air.

The activity of the present genes and gene products has been confirmed by studies showing the increase in carotenoid production in the source strain, *Methylomonas* 16a. By overexpressing genes that are early in the isoprenoid pathway, dxr and dxs, an increase in carotenoid production was observed in *Methylomonas* 16a cells. Briefly, genes dxr and dxs were overexpressed in *Methylomonas* 16a by cloning them into the low-copy, broad-host range plasmid pTJS75::lacZ:Tn5Kn (Schmidhauser and Helinsk, *J. Bacteriology*. Vol. 164:446–455 (1985)). The method for cloning genes into the host plasmid is well known in the art. Genes were amplified from the *Methylomonas* 16a genome via PCR with the following primers.

Dxs Primers

Dxs: Primer for forward reaction: aaggatccgcgtattcgtactc (contains a Bam HI site: SEQ ID NO:19).

Dxs: Primer for reverse reaction: ctggatccgatctagaaataggctcgagttgtcgttcagg (contains Bam HI and a Xho I site: SEQ ID NO:20).

Dxr Primers:

Forward reaction: aaggatcctactcgagctgacatcacagtgct (contains a Bam HI and a Xho I site: SEQ ID NO:21).

Reverse reaction: gctctagatgcaaccagaatcg (contains a Xha I site: SEQ ID NO:22).

The expected PCR product of dxs included a 323 bp sequence upstream of the start codon and the expected PCR product of dxr included 420 bp sequence upstream of the start codon in order to ensure that the natural promoters of the genes were present. First, the dxs gene was cloned into the Bam HI site, which was located between the lacZ gene and the Tn5Kn cassette of pTJS75::lacZ:Tn5Kn. The resulting plasmids were isolated from *E. coli* transformants growing on LB with kanamycin (50 µg/mL). The plasmid containing the insert in the direction of the Kn-resistance gene (as confirmed by restriction analysis) was chosen for further cloning. The dxr gene was cloned in between dxs and the Tn5Kn cassette using the Xho I and Xba I sites. The resulting plasmid is shown in FIG. 3b. The plasmid was transformed into *E. coli* using electroporation methods well known in the art. The presence of dxs and dxr in the plasmid was confirmed by restriction analysis and sequencing.

The plasmid pTJS75::dxs:dxr:lacZ:Tn5Kn was transferred from *E. coli* into *Methylomonas* 16a by triparental conjugation methods well known in the art (Rainey et al., *Mol. Gen. Genet.* (1997), 256(1), 84–87). A spontaneous rifampin (Rif)-resistant isolate of strain *Methylomonas* 16a was used as the recipient to speed the isolation of the methanotroph from contaminating *E. coli* following the mating. *E. coli* harboring the pTJS75::dxs:dxr:lacZ:Tn5Kn plasmid was the donor and *E. coli* harboring plasmid pRK2013 (Figurski and Helinski; *Proc. Natl. Acad. Sci. U.S.A.* 76:1648–1652(1979)) served as the helper. Six separately isolated kanamycin-resistant *Methylomonas* 16a transconjugants were isolated and used for the carotenoid content determination. The wild type stain and Rif resistant derivative without plasmid were used as negative controls. Six transconjugants were tested for carotenoid concentration. During the extraction, pink coloration was observed in the supernatant. The cellular carotenoid was analyzed spectrophotometrically. No qualitative differences were noticed in the spectra between negative controls and transconjugants. There were no quantitative differences between the four negative controls. There were no quantitative differences between the six transconjugants. Transconjugants have approximately a 28% increase in carotenoid concentration when compared to the negative controls (Table 3). The overproduction of dxr and dxs genes in the transconjugants is assumed to be the cause of the increase in the carotenoid production in the transconjugants. Carotenoid produced in the *Methylomonas* cells were similar in structure as in the reference strain *Methylobacterium rhodinum* as seen in HPCL analysis of saponified extract.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "mL" means milliliters, "L" means liters.

EXAMPLE 1

Isolation of *Methylomonas* 16a

The original environmental sample containing the isolate was obtained from pond sediment. The pond sediment was inoculated directly into growth medium with ammonium as nitrogen source under 25% methane in air. Methane was the sole source of carbon and energy. Growth was followed until the optical density at 660 nm was stable whereupon the culture was transferred to fresh medium such that a 1:100 dilution was achieved. After 3 successive transfers with methane as sole carbon and energy source the culture was plated onto growth agar with ammonium as nitrogen source and incubated under 25% methane in air. Many methanotrophic bacterial species were isolated in this manner. However, *Methylomonas* 16a was selected as the organism to study due to the rapid growth of colonies, large colony size, ability to grow on minimal media, and pink pigmentation indicative of an active biosynthetic pathway for carotenoids.

EXAMPLE 2

Preparation of Genomic DNA for Sequencing and Sequence Generation

Genomic DNA was isolated from *Methylomonas* according to standard protocols.

Genomic DNA and library construction were prepared according to published protocols (Friseur et al., The Minimal Gene Complement of *Mycoplasma genitalium*; Science 270, 1995). A cell pellet was resuspended in a solution containing 100 mM Na-EDTA pH 8.0, 10 mM tris-HCl pH 8.0, 400 mM NaCl, and 50 mM $MgCl_2$.

Genomic DNA preparation. After resuspension, the cells were gently lysed in 10% SDS, and incubated for 30 min at 55° C. After incubation at room temperature, proteinase K was added to 100 µg/mL and incubated at 37° C. until the suspension was clear. DNA was extracted twice with tris-equilibrated phenol and twice with chloroform. DNA was precipitated in 70% ethanol and resuspended in a solution containing 10 mM tris-HCl and 1 mM Na-EDTA (TE) pH 7.5. The DNA solution was treated with a mix of RNAases, then extracted twice with tris-equilibrated phenol and twice with chloroform. This was followed by precipitation in ethanol and resuspension in TE.

Library construction. 200 to 500 μg of chromosomal DNA was resuspended in a solution of 300 mM sodium acetate, 10 mM tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb, or 5.0 kb) was excised, cleaned and a two-step ligation procedure was used to produce a high titer library with greater than 99% single inserts.

Sequencing. A shotgun sequencing strategy approach was adopted for the sequencing of the whole microbial genome (Fleischmann, Robert et al., Whole-Genome Random sequencing and assembly of *Haemophilus influenzae* Rd Science, 269:1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc.) or the Wisconsin GCG program (Wisconsin Package Version 9.0, Genetics Computer Group (GCG), Madison, Wis.) and the CONSED package (version 7.0). All sequences represent coverage at least two times in both directions.

EXAMPLE 3

Identification and Characterization of Bacterial ORF's

ORFs encoding 1–9 were initially identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant (nr) GenBank CDS translations, sequences derived from the 3-dimensional structure Brookhaven Protein Data Bank, the SWISS-PROT protein sequence database, EMBL, and DDBJ databases). The sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTP algorithm (Altschul, S. F., et al., *Nucleic Acid Res.* 25:3389–3402) (1997) provided by the NCBI.

All initial comparisons were done using either the BLASTNnr or BLASTPnr algorithm. A refined similarity search was performed using FASTA (version 3.2) with the default parameters settings (BLOSUM 50 scoring matrix, word size ktup=2, gap penalty=–12 for the first residue and –2 for every additional residue in the gap). The results of the FASTA comparison is given in Table 1 which summarize the sequences to which they have the most similarity. Table 1 displays data based on the FASTA algorithm with values reported in expect values. The Expect value estimates the statistical significance of the match, specifying the number of matches, with a given score, that are expected in a search of a database of this size absolutely by chance.

Figure 2:
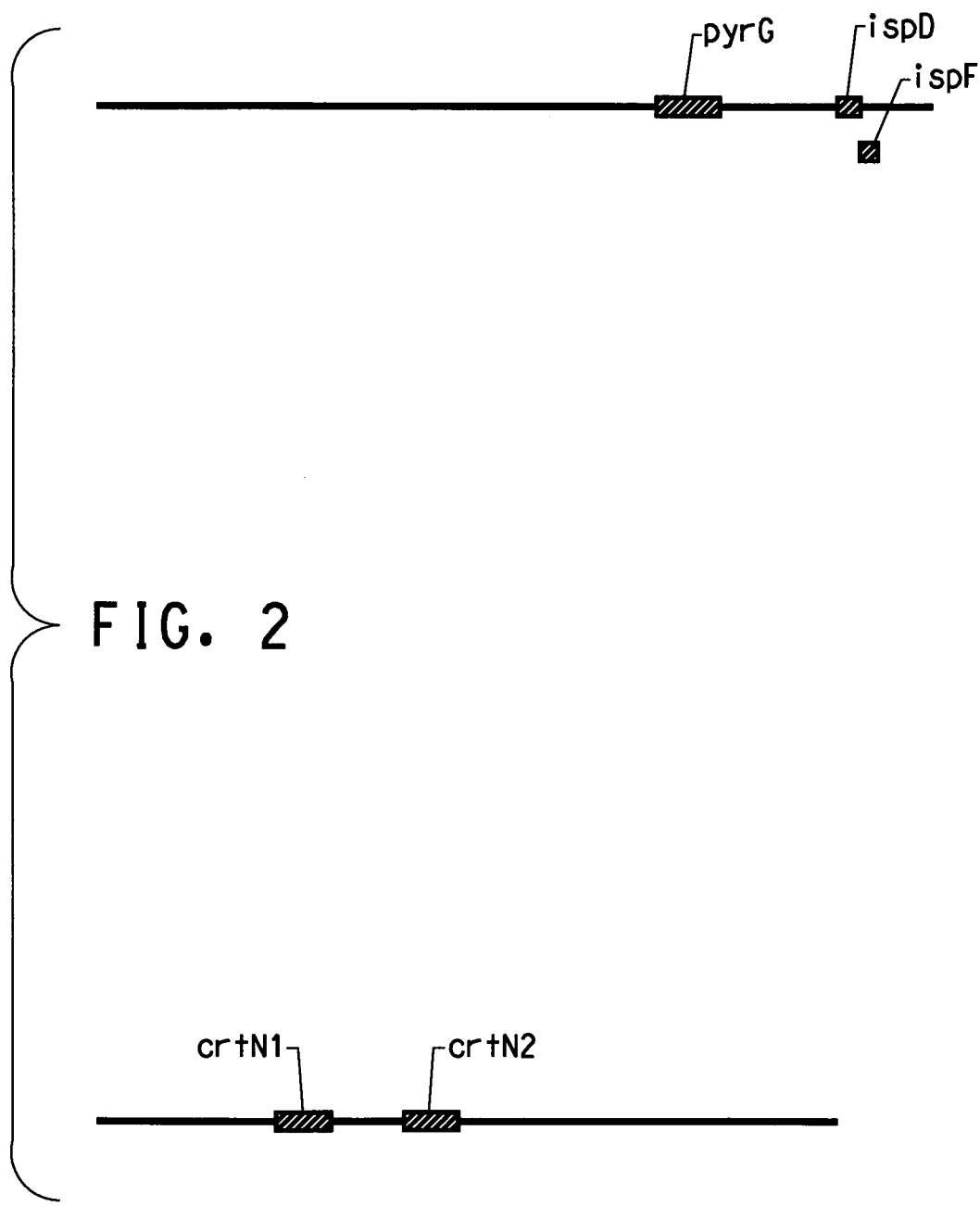
FIG. 2 shows two gene clusters contain genes in the isoprenoid pathway. One cluster contains the ispD, ispF and pyrG genes, and the other cluster contains the crtN1 and crtN2 genes.

A gene cluster of ispD, ispF and pyrG and another gene cluster of genes crtN1 and crtN2 are shown in FIG. 2.

TABLE 1

| ORF Name | Gene Name | Similarity Identified | SEQ ID | SEQ ID peptide | % Identity[a] | % Similarity[b] | E-value[c] | Citation |
|---|---|---|---|---|---|---|---|---|
| 1 | dxs | 1-deoxyxylulose-5-phosphate synthase (*E. coli*) | 1 | 2 | 60% | 86% | 5.7e–149 | Lois et al., Proc. Natl. Acad. Sci. USA. 95 (5), 2105–2110 (1998) |
| 2 | dxr | 1-deoxy-d-xylulose 5-phosphate reductoisomerase (*E. coli*) | 3 | 4 | 55% | 78% | 3.3e–74 | Takahashi et al., Proc. Natl. Acad. USA 95: 9879–9884 (1998) |
| 3 | ygbP/ispD | 2C-methyl-d-erythritol cytidylyltransferase (*E. coli*) | 5 | 6 | 52% | 74% | 7.7e–36 | Rohdich et al., Proc Natl Acad Sci USA 1999 Oct 12; 96(21): 11758–63 |
| 4 | ychB/IspE | 4-diphosphocytidyl-2-C-methylerythritol kinase (*E. coli*) | 7 | 8 | 50% | 73% | 8.8e–49 | Luttgen et al., Proc Natl Acad Sci USA. 2000 Feb 1; 97(3): 1062–7. |
| 5 | ygbB/ispF | 2C-methyl-d-erythritol 2,4-cyclodiphosphate synthase (*E. coli*) | 9 | 10 | 69% | 84% | 1.6e–36 | Herz et al., Proc Natl Acad Sci USA 2000 Mar 14; 97(6): 2486–90 |
| 6 | pyrG | CTP synthase (*E. coli*) | 11 | 12 | 67% | 89% | 2.4e–141 | Weng. et al., J. Biol. Chem. 261: 5568–5574 (1986) |
| 7 | IspA | Geranyltranstransferase (also farnesyl-diphosphate synthase) (*Synechococcus elongatus*) | 13 | 14 | 57% | 78% | 7.8e–56 | Ohto, et al., Plant Mol. Biol. 40 (2), 307–321 (1999) |
| 8 | crtN1 | diapophytoene dehydrogenase CrtN-copy 1 (*Heliobacillus mobilis*) | 15 | 16 | 34% | 72% | 4e–66 | Xiong, et al., ." Proc. Natl. Acad. Sci. U.S.A. 95 (25), 14851–14856 (1998) |
| 9 | crtN2 | Diapophytoene dehydrogenase CrtN-copy 2 (*Staphylococcus aureus*) | 17 | 18 | 49% | 78% | 1.3e–76 | Genbank #: X97985 |

TABLE 1-continued

| ORF Name | Gene Name | Similarity Identified | SEQ ID | SEQ ID peptide | % Identity[a] | % Similarity[b] | E-value[c] | Citation |
|---|---|---|---|---|---|---|---|---|
| 10 | lytB | Acinetobacter sp BD413 Putative penicillin binding protein* | 23 | 24 | 65 | 87 | 3.4e−75 | Genbank # G.I. 5915671 |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance.
% Identity, % similarity, and e-values are all reported according to FASTA analysis with Smith-Waterman computation.
*Gene function determined to be in the generation of IPP dimethylallyl diphosphate

EXAMPLE 4

Up Regulation of dxs and dxr Genes

For the cloning, the low-copy, broad-host plasmid, pTJS75::lacZ:Tn5Kn was used (Schmidhauser and Helinski *J. Bacteriology*. Vol. 164:446–455 (1985). Genes dxs and dxr were amplified from the *Methylomonas* 16a genome by using PCR with the following primers.

Dxs Primers:

Forward reaction: aaggatccgcgtattcgtactc (contains a Bam HI site, SEQ ID NO:19).

Reverse reaction: ctggatccgatctagaaataggctcgagttgtcgttcagg (contains a Bam HI and a Xho I site, SEQ ID NO:20).

Dxr Primers:

Forward reaction: aaggatcctactcgagctgacatcagtgct (contains a Bam HI and a Xho I site, SEQ ID NO:21).

Reverse reaction: gctctagatgcaaccagaatcg (contains a Xba I site, SEQ ID NO:22).

The expected PCR products of dxs and dxr genes included sequences of 323 bp and 420 bp, respectively, upstream of the start codon of each gene in order to ensure that the natural promoters of the genes were present.

| PCR program (in Perkin-Elmer, Norwalk, CT): | |
|---|---|
| Activation: | 95° C. - 900 sec |
| Cycle (35 times): | 94° C. - 45 sec |
| | 58° C. - 45 sec |
| | 72° C. - 60 sec |
| Final elongation: | 72° C. - 600 sec |

| PCR Reaction mixture: | |
|---|---|
| 25 μl | Hot Star master mix (Qiagen, Valencia, CA) |
| 0.75 μl | genomic DNA (approx. 0.1 ng) |
| 1.2 μl | sense primer (= 10 pmol) |
| 1.2 μl | antisense primer (= 10 pmol) |
| 21.85 μl | deionized water |
| 50 μl | |

Standard procedures (Sambrook, J., Fritsch, E. F. and Maniatis, T. *Molecular Cloning: A Laboratory Manual*, Second Edition, Cold Spring Harbor Laboratory Press, Cold Spring Harbor (1989)), were used in order to clone dxs and dxr into pTJS75::lacZ:Tn5Kn:

For isolation, concentration, and purification of DNA, Qiagen kits (Valencia, Calif.) were used. Enzymes for the cloning were purchased from Gibco/BRL (Rockville, Md.) or NEB (Beverly, Mass.). To transfer plasmids into *E. coli*, One Shot Top10 competent cells (Invitrogen, Carlsbad, Calif.), cuvettes (0.2 cm; Invitrogen), and Bio-Rad Gene Pulser III (Hercules, Calif.) with standard settings were used for electroporation.

TABLE 2

BTZ medium for Methylomonas 16a

| | MW | Conc. (mM) | g per L |
|---|---|---|---|
| Composition: | | | |
| NaNO$_3$ | 84.99 | 10 | 0.85 |
| KH$_2$PO$_4$ | 136.09 | 3.67 | 0.5 |
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1M HEPES (pH 7) | 238.3 | | 50 mL |
| Solution 1 | | | 10 mL |
| Solution 1 (metal solution) | | | |
| Nitriloacetic acid | 191.1 | 66.9 | 12.8 |
| CuCl$_2$ × 2H$_2$O | 170.48 | 0.15 | 0.0254 |
| FeCl$_2$ × 4H$_2$O | 198.81 | 1.5 | 0.3 |
| MnCl$_2$ × 4H$_2$O | 197.91 | 0.5 | 0.1 |
| CoCl$_2$ × 6H$_2$O | 237.9 | 1.31 | 0.312 |
| ZnCl$_2$ | 136.29 | 0.73 | 0.1 |
| H$_3$BO$_3$ | 61.83 | 0.16 | 0.01 |
| Na$_2$MoO$_4$ × 2H$_2$O | 241.95 | 0.04 | 0.01 |
| NiCl$_2$ × 6H$_2$O | 237.7 | 0.77 | 0.184 |

First, dxs was cloned into the Bam HI site, which was located between the lacZ gene and the Tn5Kn cassette of pTJS75::lacZ:Tn5Kn. The resulting plasmids were isolated from *E. coli* transformants growing on LB+ kanamycin (Kn, 50 μg/mL). The plasmid containing the insert in direction of the Kn-resistance gene (as confirmed by restriction analysis) was chosen for further cloning. Dxr gene was cloned in between dxs and Tn5Kn cassette by using the Xho I and Xba I sites. The anticipated plasmid was isolated from *E. coli* transformants. The presence of dxs and dxr in the plasmid was confirmed by restriction analysis and sequencing. The resulting plasmid, pTJS75::dxs:dxr:lacZ:Tn5Kn is shown in FIG. 3*b*.

16a Transconjugants

The plasmid pTJS75::dxs:dxr:lacZ:Tn5Kn was transferred from *E. coli* into *Methylomonas* 16a by triparental conjugation well known in the art (Rainey et al., *Mol. Gen. Genet.* (1997), 256(1), 84–87).

A spontaneous rifampin (Rif)-resistant isolate of strain *Methylomonas* 16a was used as the recipient to speed the isolation of the methanotroph from contaminating *E. coli* following the mating. *E. coli* harboring the pTJS75::dxs:dxr:lacZ:Tn5Kn plasmid was the donor and *E. coli* harboring plasmid pRK2013 (Figurski and Helinski; *Proc. Natl. Acad. Sci. U.S.A.* 76:1648–1652(1979)) served as the helper. The approximate relative cell concentrations on the plates were recipient:donor:helper=2:1:1.

The corresponding LB plates were incubated under methane (25%) at 30° C. overnight. Then the mating mixtures were scraped off the plates, resuspended in 1 mL of BTZ medium (Table 2), and plated onto BTZ plates supplemented with Rif (25 µg/mL) and Kn (50 µg/mL). The plates were incubated under methane (25%) for 7 days at 30° C. to select for *Methylomonas* 16a transconjugants. Upcoming colonies were picked and transferred to fresh selection plates for further purification. Six separately isolated kanamycin-resistant *Methylomonas* 16a transconjugants were used for carotenoid content determination.

For carotenoid determination, six 100 mL cultures of transconjugants (in BTZ+50 µg/mL Kn) were grown under methane (25%) over the weekend to stationary growth phase. Two cultures of each, the wild-type strain and its Rif-resistant derivative without the plasmid, served as a control to see whether there are different carotenoid contents in those strains and to get a standard deviation of the carotenoid determination. Cells were spun down, washed with distilled water, and freeze-dried (lyophilizer: Virtis, Gardiner, N.Y.) for 24 h in order to determine dry-weights. After the dry-weight of each culture, was determined, cells were extracted. First, cells were welled with 0.4 mL of water and let stand for 15 min. After 15 min, four mL of acetone was added and thoroughly vortexed to homogenize the sample. The samples were then shaken at 30° C. for 1 hr. After 1 hr, the cells were centrifuged. Pink coloration was observed in the supernatant. The supernatant was collected and pellets were extracted again with 0.3 mL of water and 3 mL of acetone. The supernatants from the second extraction were lighter pink in color. The supernatants of both extractions were combined, their volumes were measured, and analyzed spectrophotometrically. No qualitative differences were seen in the spectra between negative control and transconjugant samples. In acetone extract, a following observation was typical measured by spectrophotometer (shoulder at 460 nm, maxima at 491 and 522 nm) (Amersham Pharmacia Biotech, Piscataway, N.J.). For calculation of the carotenoid content, the absorption at 491 nm was read, the molar extinction coefficient of bacterioruberin (188,000) and a MW of 552 were used. The MW of the carotenoid (552 g/mol) was determined by MALDI-MS of a purified sample (Silica/Mg adsorption followed by Silica column chromatography, reference: Britton, G., Liaaen-Jensen, S., Pfander, H., Carotenoids Vol. 1a; Isolation and analysis, Birkhäuser Verlag, Basel, Boston, Berlin (1995)).

A crude acetone extract from *Methylomonas* 16a cells has a typical absorption spectrum (inflexion at 460 nm, maxima at 491 nm and 522 nm). HPLC analysis (Beckman Gold Nouveau System, Columbia, Md.; Conditions: 125×4 mm RP8 (5 µm particles) column with corresponding guard column (Hewlett-Packard, San Fernando, Calif.); flow 1 mL/min; solvent program: 0–10 min 15% water/85% methanol, then 100% methanol) of acetone extracts confirmed that one major carotenoid (net retention volume at about 6 mL) with above mentioned absorption spectrum is responsible for the pink coloration of wild-type and transconjugant *Methylomonas* 16a cells. Because nothing else in the extract absorbs at 491 nm, carotenoid content was directly measured in the acetone extract with a spectrophotometer (Amersham Pharmacia Biotech, Piscataway, N.J.).

The molar extinction coefficient of bacterioruberin (188,000), was used for the calculation of the quantity.

The following formula was used (Lambert-Beer's law) to determine the quantity of carotenoid:

$$Ca = A_{491\,nm} / (d \times \epsilon \times v \times MW)$$

Ca: Carotenoid amount (g)

$A_{491\,nm}$: Absorption of acetone extract at 491 nm (–)

d: Light path in cuvette (1 cm)

$\epsilon$: Molar extinction coefficient (L/mol×cm))

MW: Molecular weight (g/mol)

v: Volume of extract (L)

To get the carotenoid content, the calculated carotenoid amount has to be divided by the corresponding cell dry weight.

TABLE 3

Carotenoid contents in Methylomonas 16a cells

| Cultures | dry weight (mg) | carotenoid (g) | carotenoid content (µg/g) |
|---|---|---|---|
| 16a-1[a] | 30.8 | 3.00194E−06 | 97.5 |
| 16a-2[a] | 30.8 | 3.0865E−06 | 100.2 |
| 16a Rif-1[b] | 29.2 | 3.12937E−06 | 107.2 |
| 16a Rif-2[b] | 30.1 | 3.02014E−06 | 100.3 |
| dxp 1[c] | 28.2 | 3.48817E−06 | 123.7 |
| dxp 2[c] | 23.8 | 3.17224E−06 | 133.3 |
| dxp 3[c] | 31.6 | 4.01962E−06 | 127.2 |
| dxp 4[c] | 31.8 | 4.38899E−06 | 138.0 |
| dxp 5[c] | 28.4 | 3.4547E−06 | 121.6 |
| dxp 6[c] | 30.3 | 4.00817E−06 | 132.3 |

[a]Methylomonas 16a native strain
[b]Rif resistant derivative of Methylomonas 16a without plasmid
[c]transconjugants containing pTJS75::dxs:dxr:lacZ:Tn5Kn plasmid There were no significant differences between four negative controls. Likewise, there were no significant differences between six transconjugants. However, approximately 28% increase in average carotenoid production was observed in the transconjugants in comparison to the average carotenoid production in negative controls (Table 3).

In order to confirm the structure, *Methylobacterium rhodinum* (formerly *Pseudomonas rhodos*: ATCC No.14821) of which C30-carotenoid was identified was used as a reference strain (Kleinig et al., *Z. Naturforsch* 34c, 181–185 (1979); Kleinig and Schmitt, *Z. Naturforsch* 37c, 758–760 (1982)). A saponified extract of *Methylobacterium rhodinum* and of *Methylomonas* 16a were compared by HPLC analysis under the same conditions as mentioned above. The results are shown as follows: Saponified *M. rhodinum*: inflexion at 460 nm, maxima at 487 nm, 517 nm.

Net retention volume=1.9 mL.

Saponified *Methylomonas* 16a: inflexion at 460 nm, maxima at 488 nm, 518 nm.

Net retention volume=2.0 mL.

What is claimed is:

1. A method for the production of isoprenoid compounds comprising: contacting a transformed host cell under suitable growth conditions with an effective amount of a carbon source whereby an isoprenoid compound is produced, said transformed host cell comprising a nucleic acid molecule encoding SEQ ID NO: 4, under the control of suitable regulatory sequences, and wherein said isopreoid compound is selected from the group consisting of β-carotene and astaxanthin.

2. A method according to claim 1 wherein the transformed host cell is selected form the group consisting of *Aspergillus, Trichoderma, Saccharomyces, Pichia, Candida, Hansenula, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus Methanobacterium* and *Klebsiella*.

3. A method according to claim 1 wherein the carbon source is selected from the group consisting of monosaccharides, oligosaccharides, polysaccharides, carbon dioxide, methanol, methane, formaldehyde, formate, and carbon-containing amines.

4. A method according to claim 1 wherein said transformed host cell is a methanotrophic bacteria.

5. A method according to claim 1 wherein the transformed host is selected from the group consisting of *Methylomonas, Methylobacter* and *Methanobacterium* and the carbon source is selected from the group consisting of methane and methanol.

6. A method according to claim 4 wherein said methanotrophic bacteria:
   (a) grows on a C1 carbon substrate selected from the group consisting of methane and methanol; and
   (b) comprises a functional Embden-Meyerof carbon pathway, said pathway comprising a gene encoding a pyrophosphate dependent phosphofructokinase enzyme.

7. A method according to claim 6 wherein said methanotrophic bacteria is *methylomonas* 16a ATCC PTA 2402.

* * * * *

SEQUENCE LISTING

<160> NUMBER OF SEQ ID NOS: 24

<210> SEQ ID NO 1
<211> LENGTH: 1860
<212> TYPE: DNA
<213> ORGANISM: Methylomonas 16a
<220> FEATURE:
<223> OTHER INFORMATION: ORF1

<400> SEQUENCE: 1

| | | | | | |
|---|---|---|---|---|---|
| atgaaactga | ccaccgacta | tcccttgctt | aaaaacatcc | acacgccggc | ggacatacgc | 60 |
| gcgctgtcca | aggaccagct | ccagcaactg | gctgacgagg | tgcgcggcta | tctgacccac | 120 |
| acggtcagca | tttccggcgg | ccattttgcg | gccggcctcg | gcaccgtgga | actgaccgtg | 180 |
| gccttgcatt | atgtgttcaa | taccccgtc | gatcagttgg | tctgggacgt | gggccatcag | 240 |
| gcctatccgc | acaagattct | gaccggtcgc | aaggagcgca | tgccgaccat | tcgcaccctg | 300 |
| ggcggggtgt | cagcctttcc | ggcgcgggac | gagagcgaat | acgatgcctt | cggcgtcggc | 360 |
| cattccagca | cctcgatcag | cgcggcactg | ggcatggcca | ttgcgtcgca | gctgcgcggc | 420 |
| gaagacaaga | agatggtagc | catcatcggc | gacggttcca | tcaccggcgg | catggcctat | 480 |
| gaggcgatga | atcatgccgg | cgatgtgaat | gccaacctgc | tggtgatctt | gaacgacaac | 540 |
| gatatgtcga | tctcgccgcc | ggtcggggcg | atgaacaatt | atctgaccaa | ggtgttgtcg | 600 |
| agcaagtttt | attcgtcggt | gcgggaagag | agcaagaaag | ctctggccaa | gatgccgtcg | 660 |
| gtgtgggaac | tggcgcgcaa | gaccgaggaa | cacgtgaagg | gcatgatcgt | gcccggtacc | 720 |
| ttgttcgagg | aattgggctt | caattatttc | ggcccgatcg | acggccatga | tgtcgagatg | 780 |
| ctggtgtcga | ccctggaaaa | tctgaaggat | ttgaccgggc | cggtattcct | gcatgtggtg | 840 |
| accaagaagg | gcaaaggcta | tgcgccagcc | gagaaagacc | cgttggccta | ccatggcgtg | 900 |
| ccggctttcg | atccgaccaa | ggatttcctg | cccaaggcgg | cgccgtcgcc | gcatccgacc | 960 |
| tataccgagg | tgttcggccg | ctggctgtgc | gacatggcgg | ctcaagacga | gcgcttgctg | 1020 |
| ggcatcacgc | cggcgatgcg | cgaaggctct | ggtttggtgg | aattctcaca | gaaatttccg | 1080 |
| aatcgctatt | tcgatgtcgc | catcgccgag | cagcatgcgg | tgaccttggc | cgccggccag | 1140 |
| gcctgccagg | gcgccaagcc | ggtggtggcg | atttattcca | ccttcctgca | acgcggttac | 1200 |
| gatcagttga | tccacgacgt | ggccttgcag | aacttagata | tgctctttgc | actggatcgt | 1260 |
| gccggcttgg | tcgcccgga | tggaccgacc | catgctggcg | cctttgatta | cagctacatg | 1320 |
| cgctgtattc | cgaacatgct | gatcatggct | ccagccgacg | agaacgagtg | caggcagatg | 1380 |
| ctgaccaccg | gcttccaaca | ccatggcccg | gcttcggtgc | gctatccgcg | cggcaaaggg | 1440 |
| cccggggcgg | caatcgatcc | gaccctgacc | gcgctggaga | tcggcaaggc | cgaagtcaga | 1500 |
| caccacggca | gccgcatcgc | cattctggcc | tggggcagca | tggtcacgcc | tgccgtcgaa | 1560 |
| gccggcaagc | agctgggcgc | gacggtggtg | aacatgcgtt | tcgtcaagcc | gttcgatcaa | 1620 |
| gccttggtgc | tggaattggc | caggacgcac | gatgtgttcg | tcaccgtcga | ggaaaacgtc | 1680 |
| atcgccggcg | gcgctggcag | tgcgatcaac | accttcctgc | aggcgcagaa | ggtgctgatg | 1740 |
| ccggtctgca | acatcggcct | gcccgaccgc | ttcgtcgagc | aagtagtcg | cgaggaattg | 1800 |
| ctcagcctgg | tcggcctcga | cagcaagggc | atcctcgcca | ccatcgaaca | gttttgcgct | 1860 |

<210> SEQ ID NO 2
<211> LENGTH: 620

```
<212> TYPE: PRT
<213> ORGANISM: Methylomonas 16a
<220> FEATURE:
<223> OTHER INFORMATION: Amino acid sequences encoded by ORF1

<400> SEQUENCE: 2
```

Met Lys Leu Thr Thr Asp Tyr Pro Leu Leu Lys Asn Ile His Thr Pro
 1               5                  10                  15

Ala Asp Ile Arg Ala Leu Ser Lys Asp Gln Leu Gln Gln Leu Ala Asp
             20                  25                  30

Glu Val Arg Gly Tyr Leu Thr His Thr Val Ser Ile Ser Gly Gly His
         35                  40                  45

Phe Ala Ala Gly Leu Gly Thr Val Glu Leu Thr Val Ala Leu His Tyr
     50                  55                  60

Val Phe Asn Thr Pro Val Asp Gln Leu Val Trp Asp Val Gly His Gln
 65                  70                  75                  80

Ala Tyr Pro His Lys Ile Leu Thr Gly Arg Lys Glu Arg Met Pro Thr
                 85                  90                  95

Ile Arg Thr Leu Gly Gly Val Ser Ala Phe Pro Ala Arg Asp Glu Ser
            100                 105                 110

Glu Tyr Asp Ala Phe Gly Val Gly His Ser Ser Thr Ser Ile Ser Ala
        115                 120                 125

Ala Leu Gly Met Ala Ile Ala Ser Gln Leu Arg Gly Glu Asp Lys Lys
    130                 135                 140

Met Val Ala Ile Ile Gly Asp Gly Ser Ile Thr Gly Gly Met Ala Tyr
145                 150                 155                 160

Glu Ala Met Asn His Ala Gly Asp Val Asn Ala Asn Leu Leu Val Ile
                165                 170                 175

Leu Asn Asp Asn Asp Met Ser Ile Ser Pro Pro Val Gly Ala Met Asn
            180                 185                 190

Asn Tyr Leu Thr Lys Val Leu Ser Ser Lys Phe Tyr Ser Ser Val Arg
        195                 200                 205

Glu Glu Ser Lys Lys Ala Leu Ala Lys Met Pro Ser Val Trp Glu Leu
    210                 215                 220

Ala Arg Lys Thr Glu Glu His Val Lys Gly Met Ile Val Pro Gly Thr
225                 230                 235                 240

Leu Phe Glu Glu Leu Gly Phe Asn Tyr Phe Gly Pro Ile Asp Gly His
                245                 250                 255

Asp Val Glu Met Leu Val Ser Thr Leu Glu Asn Leu Lys Asp Leu Thr
            260                 265                 270

Gly Pro Val Phe Leu His Val Val Thr Lys Lys Gly Lys Gly Tyr Ala
        275                 280                 285

Pro Ala Glu Lys Asp Pro Leu Ala Tyr His Gly Val Pro Ala Phe Asp
    290                 295                 300

Pro Thr Lys Asp Phe Leu Pro Lys Ala Ala Pro Ser Pro His Pro Thr
305                 310                 315                 320

Tyr Thr Glu Val Phe Gly Arg Trp Leu Cys Asp Met Ala Ala Gln Asp
                325                 330                 335

Glu Arg Leu Leu Gly Ile Thr Pro Ala Met Arg Glu Gly Ser Gly Leu
            340                 345                 350

Val Glu Phe Ser Gln Lys Phe Pro Asn Arg Tyr Phe Asp Val Ala Ile
        355                 360                 365

Ala Glu Gln His Ala Val Thr Leu Ala Ala Gly Gln Ala Cys Gln Gly
    370                 375                 380

-continued

| | | | | | | | | | | | | |
|---|---|---|---|---|---|---|---|---|---|---|---|---|
|Ala|Lys|Pro|Val|Val|Ala|Ile|Tyr|Ser|Thr|Phe|Leu|Gln|Arg|Gly|Tyr|
|385| | | | |390| | | |395| | | | |400| |

Asp Gln Leu Ile His Asp Val Ala Leu Gln Asn Leu Asp Met Leu Phe
            405                 410                 415

Ala Leu Asp Arg Ala Gly Leu Val Gly Pro Asp Gly Pro Thr His Ala
        420                 425                 430

Gly Ala Phe Asp Tyr Ser Tyr Met Arg Cys Ile Pro Asn Met Leu Ile
            435                 440                 445

Met Ala Pro Ala Asp Glu Asn Glu Cys Arg Gln Met Leu Thr Thr Gly
    450                 455                 460

Phe Gln His His Gly Pro Ala Ser Val Arg Tyr Pro Arg Gly Lys Gly
465                 470                 475                 480

Pro Gly Ala Ala Ile Asp Pro Thr Leu Thr Ala Leu Glu Ile Gly Lys
                485                 490                 495

Ala Glu Val Arg His His Gly Ser Arg Ile Ala Ile Leu Ala Trp Gly
            500                 505                 510

Ser Met Val Thr Pro Ala Val Glu Ala Gly Lys Gln Leu Gly Ala Thr
        515                 520                 525

Val Val Asn Met Arg Phe Val Lys Pro Phe Asp Gln Ala Leu Val Leu
    530                 535                 540

Glu Leu Ala Arg Thr His Asp Val Phe Val Thr Val Glu Glu Asn Val
545                 550                 555                 560

Ile Ala Gly Gly Ala Gly Ser Ala Ile Asn Thr Phe Leu Gln Ala Gln
                565                 570                 575

Lys Val Leu Met Pro Val Cys Asn Ile Gly Leu Pro Asp Arg Phe Val
            580                 585                 590

Glu Gln Gly Ser Arg Glu Glu Leu Leu Ser Leu Val Gly Leu Asp Ser
        595                 600                 605

Lys Gly Ile Leu Ala Thr Ile Glu Gln Phe Cys Ala
    610                 615                 620

<210> SEQ ID NO 3
<211> LENGTH: 1182
<212> TYPE: DNA
<213> ORGANISM: Methylomonas 16a
<220> FEATURE:
<223> OTHER INFORMATION: ORF2

<400> SEQUENCE: 3

| | | | | |
|---|---|---|---|---|
|atgaaaggta|tttgcatatt|gggcgctacc|ggttcgatcg|gtgtcagcac|gctggatgtc|60|
|gttgccaggc|atccggataa|atatcaagtc|gttgcgctga|ccgccaacgg|caatatcgac|120|
|gcattgtatg|aacaatgcct|ggcccaccat|ccggagtatg|cggtggtggt|catgaaaagc|180|
|aaggtagcag|agttcaaaca|gcgcattgcc|gcttcgccgg|tagcggatat|caaggtcttg|240|
|tcgggtagcg|aggccttgca|acaggtggcc|acgctggaaa|acgtcgatac|ggtgatggcg|300|
|gctatcgtcg|gcgcggccgg|attgttgccg|accttggccg|cggccaaggc|cggcaaaacc|360|
|gtgctgttgg|ccaacaagga|agccttggtg|atgtcgggac|aaatcttcat|gcaggccgtc|420|
|agcgattccg|gcgctgtgtt|gctgccgata|gacagcgagc|acaacgccat|ctttcagtgc|480|
|atgccggcgg|gttatacgcc|aggccataca|gccaaacagg|cgcgccgcat|tttattgacc|540|
|gcttccggtg|gcccatttcg|acggacgccg|atagaaacgt|tgtccagcgt|cacgccggat|600|
|caggccgttg|cccatcctaa|atgggacatg|gggcgcaaga|tttcggtcga|ttccgccacc|660|
|atgatgaaca|aaggtctcga|actgatcgaa|gcctgccttg|tgttcaacat|ggagcccgac|720|

-continued

```
cagattgaag tcgtcattca tccgcagagc atcattcatt cgatggtgga ctatgtcgat    780
ggttcggttt tggcgcagat gggtaatccc gacatgcgca cgccgatagc gcacgcgatg    840
gcctggccgg aacgctttga ctctggtgtg gcgccgctgg atattttcga agtagggcac    900
atggatttcg aaaaacccga cttgaaacgg tttccttgtc tgagattggc ttatgaagcc    960
atcaagtctg gtggaattat gccaacggta ttgaacgcag ccaatgaaat tgctgtcgaa   1020 gcgttttttaa atgaagaagt caaattcact gacatcgcgg tcatcatcga agcgcagcatg  1080 gcccagttta accggacga tgccggcagc ctcgaattgg ttttgcaggc cgatcaagat   1140
gcgcgcgagg tggctagaga catcatcaag accttggtag ct                      1182
```

<210> SEQ ID NO 4
<211> LENGTH: 394
<212> TYPE: PRT
<213> ORGANISM: Methylomonas 16a
<220> FEATURE:
<223> OTHER INFORMATION: Amino acid sequences encoded by ORF2

<400> SEQUENCE: 4

```
Met Lys Gly Ile Cys Ile Leu Gly Ala Thr Gly Ser Ile Gly Val Ser
  1               5                  10                  15

Thr Leu Asp Val Val Ala Arg His Pro Asp Lys Tyr Gln Val Val Ala
                 20                  25                  30

Leu Thr Ala Asn Gly Asn Ile Asp Ala Leu Tyr Glu Gln Cys Leu Ala
             35                  40                  45

His His Pro Glu Tyr Ala Val Val Met Glu Ser Lys Val Ala Glu
         50                  55                  60

Phe Lys Gln Arg Ile Ala Ala Ser Pro Val Ala Asp Ile Lys Val Leu
 65                  70                  75                  80

Ser Gly Ser Glu Ala Leu Gln Gln Val Ala Thr Leu Glu Asn Val Asp
                 85                  90                  95

Thr Val Met Ala Ala Ile Val Gly Ala Ala Gly Leu Leu Pro Thr Leu
            100                 105                 110

Ala Ala Ala Lys Ala Gly Lys Thr Val Leu Leu Ala Asn Lys Glu Ala
            115                 120                 125

Leu Val Met Ser Gly Gln Ile Phe Met Gln Ala Val Ser Asp Ser Gly
        130                 135                 140

Ala Val Leu Leu Pro Ile Asp Ser Glu His Asn Ala Ile Phe Gln Cys
145                 150                 155                 160

Met Pro Ala Gly Tyr Thr Pro Gly His Thr Ala Lys Gln Ala Arg Arg
                165                 170                 175

Ile Leu Leu Thr Ala Ser Gly Gly Pro Phe Arg Arg Thr Pro Ile Glu
            180                 185                 190

Thr Leu Ser Ser Val Thr Pro Asp Gln Ala Val Ala His Pro Lys Trp
        195                 200                 205

Asp Met Gly Arg Lys Ile Ser Val Asp Ser Ala Thr Met Met Asn Lys
    210                 215                 220

Gly Leu Glu Leu Ile Glu Ala Cys Leu Leu Phe Asn Met Glu Pro Asp
225                 230                 235                 240

Gln Ile Glu Val Val Ile His Pro Gln Ser Ile Ile His Ser Met Val
                245                 250                 255

Asp Tyr Val Asp Gly Ser Val Leu Ala Gln Met Gly Asn Pro Asp Met
            260                 265                 270

Arg Thr Pro Ile Ala His Ala Met Ala Trp Pro Glu Arg Phe Asp Ser
        275                 280                 285
```

```
Gly Val Ala Pro Leu Asp Ile Phe Glu Val Gly His Met Asp Phe Glu
        290                 295                 300

Lys Pro Asp Leu Lys Arg Phe Pro Cys Leu Arg Leu Ala Tyr Glu Ala
305                 310                 315                 320

Ile Lys Ser Gly Gly Ile Met Pro Thr Val Leu Asn Ala Ala Asn Glu
            325                 330                 335

Ile Ala Val Glu Ala Phe Leu Asn Glu Glu Val Lys Phe Thr Asp Ile
            340                 345                 350

Ala Val Ile Ile Glu Arg Ser Met Ala Gln Phe Lys Pro Asp Asp Ala
            355                 360                 365

Gly Ser Leu Glu Leu Val Leu Gln Ala Asp Gln Asp Ala Arg Glu Val
        370                 375                 380

Ala Arg Asp Ile Ile Lys Thr Leu Val Ala
385                 390
```

<210> SEQ ID NO 5
<211> LENGTH: 693
<212> TYPE: DNA
<213> ORGANISM: Methylomonas 16a
<220> FEATURE:
<223> OTHER INFORMATION: ORF3

<400> SEQUENCE: 5

```
atgaacccaa ccatccaatg ctgggccgtc gtgcccgcag ccggcgtcgg caaacgcatg     60
caagccgatc gccccaaaca atatttaccg cttgccggta aaacggtcat cgaacacaca    120
ctgactcgac tacttgagtc cgacgccttc caaaaagttg cggtggcgat tccgtcgaa    180
gacccttatt ggcctgaact gtccatagcc aaacaccccg acatcatcac cgcgcctggc    240
ggcaaggaac gcgccgactc ggtgctgtct gcactgaagg ctttagaaga tatagccagc    300
gaaaatgatt gggtgctggt acacgacgcc gcccgccect gcttgacggg cagcgacatc    360
caccttcaaa tcgataccett aaaaaatgac ccggtcggcg gcatcctggc cttgagttcg    420
cacgacacat tgaaacacgt ggatggtgac acgatcaccg caaccataga cagaaagcac    480
gtctggcgcg ccttgacgcc gcaaatgttc aaatacggca tgttgcgcga cgcgttgcaa    540
cgaaccgaag gcaatccggc cgtcaccgac gaagccagtg cgctggaact ttgggccat    600
aaacccaaaa tcgtggaagg ccgcccggac aacatcaaaa tcacccgccc ggaagatttg    660
gccctggcac aattttatat ggagcaacaa gca                                 693
```

<210> SEQ ID NO 6
<211> LENGTH: 231
<212> TYPE: PRT
<213> ORGANISM: Methylomonas 16a
<220> FEATURE:
<223> OTHER INFORMATION: Amino acid sequences encoded by ORF3

<400> SEQUENCE: 6

```
Met Asn Pro Thr Ile Gln Cys Trp Ala Val Val Pro Ala Ala Gly Val
  1               5                  10                  15

Gly Lys Arg Met Gln Ala Asp Arg Pro Lys Gln Tyr Leu Pro Leu Ala
             20                  25                  30

Gly Lys Thr Val Ile Glu His Thr Leu Thr Arg Leu Leu Glu Ser Asp
         35                  40                  45

Ala Phe Gln Lys Val Ala Val Ala Ile Ser Val Glu Asp Pro Tyr Trp
     50                  55                  60

Pro Glu Leu Ser Ile Ala Lys His Pro Asp Ile Ile Thr Ala Pro Gly
```

```
             65                  70                  75                  80
Gly Lys Glu Arg Ala Asp Ser Val Leu Ser Ala Leu Lys Ala Leu Glu
                     85                  90                  95

Asp Ile Ala Ser Glu Asn Asp Trp Val Leu Val His Asp Ala Ala Arg
                100                 105                 110

Pro Cys Leu Thr Gly Ser Asp Ile His Leu Gln Ile Asp Thr Leu Lys
            115                 120                 125

Asn Asp Pro Val Gly Gly Ile Leu Ala Leu Ser Ser His Asp Thr Leu
        130                 135                 140

Lys His Val Asp Gly Asp Thr Ile Thr Ala Thr Ile Asp Arg Lys His
145                 150                 155                 160

Val Trp Arg Ala Leu Thr Pro Gln Met Phe Lys Tyr Gly Met Leu Arg
                165                 170                 175

Asp Ala Leu Gln Arg Thr Glu Gly Asn Pro Ala Val Thr Asp Glu Ala
                180                 185                 190

Ser Ala Leu Glu Leu Leu Gly His Lys Pro Lys Ile Val Glu Gly Arg
            195                 200                 205

Pro Asp Asn Ile Lys Ile Thr Arg Pro Glu Asp Leu Ala Leu Ala Gln
        210                 215                 220

Phe Tyr Met Glu Gln Gln Ala
225                 230
```

<210> SEQ ID NO 7
<211> LENGTH: 855
<212> TYPE: DNA
<213> ORGANISM: Methylomonas 16a
<220> FEATURE:
<223> OTHER INFORMATION: ORF4

<400> SEQUENCE: 7

```
atggattatg cggctgggtg gggcgaaaga tggcctgctc cggcaaaatt gaacttaatg      60
ttgaggatta ccggtcgcag gccagatggc tatcatctgt tgcaaacggt gtttcaaatg    120
ctcgatctat gcgattggtt gacgtttcat ccggttgatg atggccgcgt gacgctgcga    180
aatccaatct ccggcgttcc agagcaggat gacttgactg ttcgggcggc taatttgttg    240
aagtctcata ccggctgtgt gcgcggagtt tgtatcgata tcgagaaaaa tctgcctatg    300
ggtggtggtt tgggtggtgg aagttccgat gctgctacaa ccttggtagt tctaaatcgg    360
ctttggggct tgggcttgtc gaagcgtgag ttgatggatt tgggcttgag gcttggtgcc    420
gatgtgcctg tgtttgtgtt tggttgttcg gcctggggcg aagtgtgagc gaggatttg     480
caggcaataa cgttgccgga caatggtttt gtcatcatta accggattgc catgtgaat     540
actgagaaa ttttttctgc agaaaatttg acaaggaata gtgcagtcgt tacaatgagc    600
gactttcttg cagggataa tcggaatgat tgttcggaag tggtttgcaa gttatatcga    660
ccggtgaaag atgcaatcga tgcgttgtta tgctatgcgg aagcgagatt gacggggacc    720
ggtgcatgtg tgttcgctca gttttgtaac aaggaagatg ctgagagtgc gttagaagga    780
ttgaaagatc ggtggctggt gttcttggct aaaggcttga atcagtctgc gctctacaag    840
aaattagaac aggga                                                     855
```

<210> SEQ ID NO 8
<211> LENGTH: 285
<212> TYPE: PRT
<213> ORGANISM: Methylomonas 16a
<220> FEATURE:
<223> OTHER INFORMATION: Amino acid sequences encoded by ORF4

<400> SEQUENCE: 8

| | | | | | | | | | | | | | | |
|---|---|---|---|---|---|---|---|---|---|---|---|---|---|---|
|Met|Asp|Tyr|Ala|Ala|Gly|Trp|Gly|Glu|Arg|Trp|Pro|Ala|Pro|Ala|Lys
|1| | | |5| | | | |10| | | | |15|

Leu Asn Leu Met Leu Arg Ile Thr Gly Arg Arg Pro Asp Gly Tyr His
                20                  25                  30

Leu Leu Gln Thr Val Phe Gln Met Leu Asp Leu Cys Asp Trp Leu Thr
            35                  40                  45

Phe His Pro Val Asp Asp Gly Arg Val Thr Leu Arg Asn Pro Ile Ser
        50                  55                  60

Gly Val Pro Glu Gln Asp Asp Leu Thr Val Arg Ala Ala Asn Leu Leu
65                  70                  75                  80

Lys Ser His Thr Gly Cys Val Arg Gly Val Cys Ile Asp Ile Glu Lys
                85                  90                  95

Asn Leu Pro Met Gly Gly Gly Leu Gly Gly Ser Ser Asp Ala Ala
                100                 105                 110

Thr Thr Leu Val Val Leu Asn Arg Leu Trp Gly Leu Gly Leu Ser Lys
            115                 120                 125

Arg Glu Leu Met Asp Leu Gly Leu Arg Leu Gly Ala Asp Val Pro Val
        130                 135                 140

Phe Val Phe Gly Cys Ser Ala Trp Gly Glu Gly Val Ser Glu Asp Leu
145                 150                 155                 160

Gln Ala Ile Thr Leu Pro Glu Gln Trp Phe Val Ile Ile Lys Pro Asp
                165                 170                 175

Cys His Val Asn Thr Gly Glu Ile Phe Ser Ala Glu Asn Leu Thr Arg
            180                 185                 190

Asn Ser Ala Val Val Thr Met Ser Asp Phe Leu Ala Gly Asp Asn Arg
        195                 200                 205

Asn Asp Cys Ser Glu Val Val Cys Lys Leu Tyr Arg Pro Val Lys Asp
        210                 215                 220

Ala Ile Asp Ala Leu Leu Cys Tyr Ala Glu Ala Arg Leu Thr Gly Thr
225                 230                 235                 240

Gly Ala Cys Val Phe Ala Gln Phe Cys Asn Lys Glu Asp Ala Glu Ser
                245                 250                 255

Ala Leu Glu Gly Leu Lys Asp Arg Trp Leu Val Phe Leu Ala Lys Gly
                260                 265                 270

Leu Asn Gln Ser Ala Leu Tyr Lys Lys Leu Glu Gln Gly
            275                 280                 285

<210> SEQ ID NO 9
<211> LENGTH: 471
<212> TYPE: DNA
<213> ORGANISM: Methylomonas 16a
<220> FEATURE:
<223> OTHER INFORMATION: ORF5

<400> SEQUENCE: 9
atgatacgcg taggcatggg ttacgacgtg caccgtttca acgacggcga ccacatcatt    60
ttgggcggcg tcaaaatccc ttatgaaaaa ggcctggaag cccattccga cggcgacgtg   120
gtgctgcacg cattggccga cgccatcttg ggagccgccg ctttgggcga catcggcaaa   180
catttcccgg acaccgaccc caatttcaag ggcgccgaca gcaggggtgct actgcgccac   240 gtgtacggca tcgtcaagga aaaaggctat aaactggtca acgccgacgt gaccatcatc   300
gctcaggcgc cgaagatgct gccacacgtg cccggcatgc gcgccaacat tgccgccgat   360

```
ctggaaaccg atgtcgattt cattaatgta aaagccacga cgaccgagaa actgggcttt    420
gagggccgta aggaaggcat cgccgtgcag gctgtggtgt tgatagaacg c             471
```

<210> SEQ ID NO 10
<211> LENGTH: 157
<212> TYPE: PRT
<213> ORGANISM: Methylomonas 16a
<220> FEATURE:
<223> OTHER INFORMATION: Amino acid sequences encoded by ORF5

<400> SEQUENCE: 10

```
Met Ile Arg Val Gly Met Gly Tyr Asp Val His Arg Phe Asn Asp Gly
 1               5                  10                  15

Asp His Ile Ile Leu Gly Gly Val Lys Ile Pro Tyr Glu Lys Gly Leu
                20                  25                  30

Glu Ala His Ser Asp Gly Asp Val Val Leu His Ala Leu Ala Asp Ala
            35                  40                  45

Ile Leu Gly Ala Ala Ala Leu Gly Asp Ile Gly Lys His Phe Pro Asp
        50                  55                  60

Thr Asp Pro Asn Phe Lys Gly Ala Asp Ser Arg Val Leu Leu Arg His
    65                  70                  75                  80

Val Tyr Gly Ile Val Lys Glu Lys Gly Tyr Lys Leu Val Asn Ala Asp
                85                  90                  95

Val Thr Ile Ile Ala Gln Ala Pro Lys Met Leu Pro His Val Pro Gly
                100                 105                 110

Met Arg Ala Asn Ile Ala Ala Asp Leu Glu Thr Asp Val Asp Phe Ile
            115                 120                 125

Asn Val Lys Ala Thr Thr Thr Glu Lys Leu Gly Phe Glu Gly Arg Lys
        130                 135                 140

Glu Gly Ile Ala Val Gln Ala Val Val Leu Ile Glu Arg
145                 150                 155
```

<210> SEQ ID NO 11
<211> LENGTH: 1632
<212> TYPE: DNA
<213> ORGANISM: Methylomonas 16a
<220> FEATURE:
<223> OTHER INFORMATION: ORF6

<400> SEQUENCE: 11

```
atgacaaaat tcatctttat caccggcggc gtggtgtcat ccttgggaaa agggatagcc    60
gcctcctccc tggcggcgat tctggaagac gcgggcctca agtcactat cacaaaactc    120 gatccctaca tcaacgtcga ccccggcacc atgagcccgt tcaacacgg cgaggtgttc    180 gtgaccgaag acggtgccga aaccgatttg gaccttggcc attacgaacg gttttttgaaa   240 accacgatga ccaagaaaaa caacttcacc accggtcagg tttacgagca ggtattacgc   300
aacgagcgca aggtgattta tcttggcgcg accgtgcaag tcattccaca tatcaccgac   360
gaaatcaaac gccgggtgta tgaaagcgcc gaagggaaag atgtggcatt gatcgaagtc   420
ggcggcacgg tgggcgacat cgaatcgtta ccgtttctgg aaaccatacg ccagatgggc   480
gtggaactgg gtcgtgaccg cgccttgttc attcatttga cgctggtgcc ttacatcaaa   540
tcggccggcg aactgaaaac caagcccacc cagcattcgg tcaaagaact gcgcaccatc   600
gggattcagc cggacatttt gatctgtcgt tcagaacaac cgatcccggc cagtgaacgc   660
cgcaagatcg cgctatttac caatgtcgcc gaaaaggcgg tgatttccgc gatcgatgcc   720
gacaccattt accgcattcc gctattgctg cgcgaacaag gcctggacga cctggtggtc   780
```

```
gatcagttgc gcctggacgt accagcggcg gatttatcgg cctgggaaaa ggtcgtcgat    840
ggcctgactc atccgaccga cgaagtcagc attgcgatcg tcggtaaata tgtcgaccac    900
accgatgcct acaaatcgct gaatgaagcc ctgattcatg ccggcattca cacgcgccac    960
aaggtgcaaa tcagctacat cgactccgaa accatagaag ccgaaggcac cgccaaattg   1020
aaaaacgtcg atgcgatcct ggtgccgggt ggtttcggcg aacgcggcgt ggaaggcaag   1080
atttctaccg tgcgttttgc ccgcgagaac aaaatcccgt atttgggcat ttgcttgggc   1140
atgcaatcgg cggtaatcga attcgcccgc aacgtggttg gcctggaagg cgcgcacagc   1200
accgaattcc tgccgaaatc gccacaccct gtgatcggct tgatcaccga atggatggac   1260
gaagccggcg aactggtcac acgcgacgaa gattccgatc tgggcggcac gatgcgtctg   1320
ggcgcgcaaa atgccgcct gaaggctgat tccttggctt ttcagttgta tcaaaaagac   1380
gtcatcaccg agcgtcaccg ccaccgctac gaattcaaca atcaatattt aaaacaactg   1440
gaagcggccg gcatgaaatt ttccggtaaa tcgctggacg gccgcctggt ggagatcatc   1500
gagctacccg aacaccctg gttcctggcc tgccagttcc atcccgaatt cacctcgacg   1560
ccgcgtaacg gccacgccct attttcgggc ttcgtcgaag cggccgccaa acacaaaaca   1620
caaggcacag ca                                                       1632
```

<210> SEQ ID NO 12
<211> LENGTH: 544
<212> TYPE: PRT
<213> ORGANISM: Methylomonas 16a
<220> FEATURE:
<223> OTHER INFORMATION: Amino acid sequences encoded by ORF6

<400> SEQUENCE: 12

```
Met Thr Lys Phe Ile Phe Ile Thr Gly Gly Val Val Ser Ser Leu Gly
 1               5                  10                  15

Lys Gly Ile Ala Ala Ser Ser Leu Ala Ala Ile Leu Glu Asp Arg Gly
            20                  25                  30

Leu Lys Val Thr Ile Thr Lys Leu Asp Pro Tyr Ile Asn Val Asp Pro
        35                  40                  45

Gly Thr Met Ser Pro Phe Gln His Gly Glu Val Phe Val Thr Glu Asp
    50                  55                  60

Gly Ala Glu Thr Asp Leu Asp Leu Gly His Tyr Glu Arg Phe Leu Lys
65                  70                  75                  80

Thr Thr Met Thr Lys Lys Asn Asn Phe Thr Thr Gly Gln Val Tyr Glu
                85                  90                  95

Gln Val Leu Arg Asn Glu Arg Lys Gly Asp Tyr Leu Gly Ala Thr Val
            100                 105                 110

Gln Val Ile Pro His Ile Thr Asp Glu Ile Lys Arg Arg Val Tyr Glu
        115                 120                 125

Ser Ala Glu Gly Lys Asp Val Ala Leu Ile Glu Val Gly Gly Thr Val
    130                 135                 140

Gly Asp Ile Glu Ser Leu Pro Phe Leu Glu Thr Ile Arg Gln Met Gly
145                 150                 155                 160

Val Glu Leu Gly Arg Asp Arg Ala Leu Phe Ile His Leu Thr Leu Val
                165                 170                 175

Pro Tyr Ile Lys Ser Ala Gly Glu Leu Lys Thr Lys Pro Thr Gln His
            180                 185                 190

Ser Val Lys Glu Leu Arg Thr Ile Gly Ile Gln Pro Asp Ile Leu Ile
        195                 200                 205
```

```
Cys Arg Ser Glu Gln Pro Ile Pro Ala Ser Glu Arg Arg Lys Ile Ala
        210                 215                 220
Leu Phe Thr Asn Val Ala Glu Lys Ala Val Ile Ser Ala Ile Asp Ala
225                 230                 235                 240
Asp Thr Ile Tyr Arg Ile Pro Leu Leu Leu Arg Glu Gln Gly Leu Asp
                245                 250                 255
Asp Leu Val Val Asp Gln Leu Arg Leu Asp Val Pro Ala Ala Asp Leu
                260                 265                 270
Ser Ala Trp Glu Lys Val Val Asp Gly Leu Thr His Pro Thr Asp Glu
            275                 280                 285
Val Ser Ile Ala Ile Val Gly Lys Tyr Val Asp His Thr Asp Ala Tyr
        290                 295                 300
Lys Ser Leu Asn Glu Ala Leu Ile His Ala Gly Ile His Thr Arg His
305                 310                 315                 320
Lys Val Gln Ile Ser Tyr Ile Asp Ser Glu Thr Ile Glu Ala Glu Gly
                325                 330                 335
Thr Ala Lys Leu Lys Asn Val Asp Ala Ile Leu Val Pro Gly Gly Phe
            340                 345                 350
Gly Glu Arg Gly Val Glu Gly Lys Ile Ser Thr Val Arg Phe Ala Arg
        355                 360                 365
Glu Asn Lys Ile Pro Tyr Leu Gly Ile Cys Leu Gly Met Gln Ser Ala
370                 375                 380
Val Ile Glu Phe Ala Arg Asn Val Val Gly Leu Glu Gly Ala His Ser
385                 390                 395                 400
Thr Glu Phe Leu Pro Lys Ser Pro His Pro Val Ile Gly Leu Ile Thr
                405                 410                 415
Glu Trp Met Asp Glu Ala Gly Glu Leu Val Thr Arg Asp Glu Asp Ser
            420                 425                 430
Asp Leu Gly Gly Thr Met Arg Leu Gly Ala Gln Lys Cys Arg Leu Lys
        435                 440                 445
Ala Asp Ser Leu Ala Phe Gln Leu Tyr Gln Lys Asp Val Ile Thr Glu
450                 455                 460
Arg His Arg His Arg Tyr Glu Phe Asn Asn Gln Tyr Leu Lys Gln Leu
465                 470                 475                 480
Glu Ala Ala Gly Met Lys Phe Ser Gly Lys Ser Leu Asp Gly Arg Leu
                485                 490                 495
Val Glu Ile Ile Glu Leu Pro Glu His Pro Trp Phe Leu Ala Cys Gln
            500                 505                 510
Phe His Pro Glu Phe Thr Ser Thr Pro Arg Asn Gly His Ala Leu Phe
        515                 520                 525
Ser Gly Phe Val Glu Ala Ala Lys His Lys Thr Gln Gly Thr Ala
    530                 535                 540

<210> SEQ ID NO 13
<211> LENGTH: 891
<212> TYPE: DNA
<213> ORGANISM: Methylomonas 16a
<220> FEATURE:
<223> OTHER INFORMATION: ORF7

<400> SEQUENCE: 13
atgagtaaat tgaaagccta cctgaccgtc tgccaagaac gcgtcgagcg cgcgctggac      60
gcccgtctgc ctgccgaaaa catactgcca caaaccttgc atcaggccat gcgctattcc     120
gtattgaacg gcggcaaacg cacccggccc ttgttgactt atgcgaccgg tcaggctttg     180
```

-continued

```
ggcttgccgg aaaacgtgct ggatgcgccg gcttgcgcgg tagaattcat ccatgtgtat    240
tcgctgattc acgacgatct gccggccatg acaacgatg atctgcgccg cggcaaaccg    300
acctgtcaca aggcttacga cgaggccacc gccattttgg ccggcgacgc actgcaggcg    360
ctggcctttg aagttctggc caacgacccc ggcatcaccg tcgatgcccc ggctcgcctg    420
aaaatgatca cggctttgac ccgcgccagc ggctctcaag gcatggtggg cggtcaagcc    480
atcgatctcg gctccgtcgg ccgcaaattg acgctgccgg aactcgaaaa catgcatatc    540
cacaagactg gcgccctgat ccgcgccagc gtcaatctgg cggcattatc caaacccgat    600
ctggatactt gcgtcgccaa gaaactggat cactatgcca aatgcatagg cttgtcgttc    660
caggtcaaag acgacattct cgacatcgaa gccgacaccg cgacactcgg caagactcag    720
ggcaaggaca tcgataacga caaaccgacc taccctgcgc tattgggcat ggctggcgcc    780
aaacaaaaag cccaggaatt gcacgaacaa gcagtcgaaa gcttaacggg atttggcagc    840
gaagccgacc tgctgcgcga actatcgctt tacatcatcg agcgcacgca c             891
```

<210> SEQ ID NO 14
<211> LENGTH: 297
<212> TYPE: PRT
<213> ORGANISM: Methylomonas 16a
<220> FEATURE:
<223> OTHER INFORMATION: Amino acid sequences encoded by ORF7

<400> SEQUENCE: 14

```
Met Ser Lys Leu Lys Ala Tyr Leu Thr Val Cys Gln Glu Arg Val Glu
 1               5                  10                  15

Arg Ala Leu Asp Ala Arg Leu Pro Ala Glu Asn Ile Leu Pro Gln Thr
            20                  25                  30

Leu His Gln Ala Met Arg Tyr Ser Val Leu Asn Gly Gly Lys Arg Thr
        35                  40                  45

Arg Pro Leu Leu Thr Tyr Ala Thr Gly Gln Ala Leu Gly Leu Pro Glu
    50                  55                  60

Asn Val Leu Asp Ala Pro Ala Cys Ala Val Glu Phe Ile His Val Tyr
65                  70                  75                  80

Ser Leu Ile His Asp Asp Leu Pro Ala Met Asp Asn Asp Asp Leu Arg
                85                  90                  95

Arg Gly Lys Pro Thr Cys His Lys Ala Tyr Asp Glu Ala Thr Ala Ile
            100                 105                 110

Leu Ala Gly Asp Ala Leu Gln Ala Leu Ala Phe Glu Val Leu Ala Asn
        115                 120                 125

Asp Pro Gly Ile Thr Val Asp Ala Pro Ala Arg Leu Lys Met Ile Thr
    130                 135                 140

Ala Leu Thr Arg Ala Ser Gly Ser Gln Gly Met Val Gly Gly Gln Ala
145                 150                 155                 160

Ile Asp Leu Gly Ser Val Gly Arg Lys Leu Thr Leu Pro Glu Leu Glu
                165                 170                 175

Asn Met His Ile His Lys Thr Gly Ala Leu Ile Arg Ala Ser Val Asn
            180                 185                 190

Leu Ala Ala Leu Ser Lys Pro Asp Leu Asp Thr Cys Val Ala Lys Lys
        195                 200                 205

Leu Asp His Tyr Ala Lys Cys Ile Gly Leu Ser Phe Gln Val Lys Asp
    210                 215                 220

Asp Ile Leu Asp Ile Glu Ala Asp Thr Ala Thr Leu Gly Lys Thr Gln
225                 230                 235                 240
```

Gly Lys Asp Ile Asp Asn Asp Lys Pro Thr Tyr Pro Ala Leu Leu Gly
            245                 250                 255

Met Ala Gly Ala Lys Gln Lys Ala Gln Glu Leu His Glu Gln Ala Val
        260                 265                 270

Glu Ser Leu Thr Gly Phe Gly Ser Glu Ala Asp Leu Leu Arg Glu Leu
    275                 280                 285

Ser Leu Tyr Ile Ile Glu Arg Thr His
    290                 295

<210> SEQ ID NO 15
<211> LENGTH: 1533
<212> TYPE: DNA
<213> ORGANISM: Methylomonas 16a
<220> FEATURE:
<223> OTHER INFORMATION: ORF8

<400> SEQUENCE: 15

```
atggccaaca ccaaacacat catcatcgtc ggcgcgggtc ccggcggact ttgcgccggc      60
atgttgctga ccagcgcgg cttcaaggta tcgattttcg acaaacatgc agaaatcggc     120
ggccgcaacc gcccgatcaa catgaacggc tttaccttcg ataccggtcc gacattcttg     180
ttgatgaaag gcgtgctgga cgaaatgttc gaactgtgcg agcgccgtag cgaggattat     240
ctggaattcc tgccgctaag cccgatgtac cgcctgctgt acgacgaccg cgacatcttc     300
gtctattccg accgcagaa catgcgcgcc gaattgcaac gggtattcga cgaaggcacg     360
gacggctacg aacagttcat ggaacaggaa cgcaaacgct tcaacgcgct gtatccctgc     420
atcacccgcg attattccag cctgaaatcc tttttgtcgc tggacttgat caaggccctg     480
ccgtggctgg cttttccgaa aagcgtgttc aataatctcg ccagtatttt caaccaggaa     540
aaaatgcgcc tggccttttg ctttcagtcc aagtatctgg gcatgtcgcc gtgggaatgc     600
ccggcactgt ttacgatgct gccctatctg gagcacgaat acggcattta tcacgtcaaa     660
ggcggcctga accgcatcgc ggcggcgatg gcgcaagtga tcgcggaaaa cggcggcgaa     720
attcacttga cagcgaaat cgagtcgctg atcatcgaaa acggcgctgc caagggcgtc     780
aaattacaac atggcgcgga gctgcgcggc gacgaagtca tcatcaacgc ggattttgcc     840
cacgcgatga cgcatctggt caaaccgggc gtcttgaaaa aatacacccc ggaaaacctg     900
aagcagcgcg agtattcctg ttcgaccttc atgctgtatc tgggtttgga caagatttac     960
gatctgccgc accataccat cgtgtttgcc aaggattaca ccaccaatat ccgcaacatt    1020
ttcgacaaca aaaccctgac ggacgatttt tcgtttttacg tgcaaaacgc cagcgccagc    1080
gacgacagcc tagcgccagc cggcaaatcg gcgctgtacg tgctggtgcc gatgcccaac    1140
aacgacagcg gcctggactg gcaggcgcat tgccaaaacg tgcgcgaaca ggtgttggac    1200
acgctgggcg cgcgactggg attgagcgac atcagagccc atatcgaatg cgaaaaaatc    1260
atcacgccgc aaacctggga acggacgaa cacgtttaca agggcgccac tttcagtttg    1320
tcgcacaagt tcagccaaat gctgtactgg cggccgcaca accgtttcga ggaactggcc    1380
aattgctatc tggtcggcgg cggcacgcat cccggtagcg gtttgccgac catctacgaa    1440
tcggcgcgga tttcggccaa gctgattttcc cagaaacatc gggtgaggtt caaggacata    1500
gcacacagcg cctggctgaa aaaagccaaa gcc                                 1533
```

<210> SEQ ID NO 16
<211> LENGTH: 511
<212> TYPE: PRT

<213> ORGANISM: Methylomonas 16a
<220> FEATURE:
<223> OTHER INFORMATION: Amino acid sequences encoded by ORF8

<400> SEQUENCE: 16

```
Met Ala Asn Thr Lys His Ile Ile Val Gly Ala Gly Pro Gly Gly
  1               5                  10                  15

Leu Cys Ala Gly Met Leu Leu Ser Gln Arg Gly Phe Lys Val Ser Ile
             20                  25                  30

Phe Asp Lys His Ala Glu Ile Gly Gly Arg Asn Arg Pro Ile Asn Met
             35                  40                  45

Asn Gly Phe Thr Phe Asp Thr Gly Pro Thr Phe Leu Leu Met Lys Gly
 50                  55                  60

Val Leu Asp Glu Met Phe Glu Leu Cys Glu Arg Arg Ser Glu Asp Tyr
 65                  70                  75                  80

Leu Glu Phe Leu Pro Leu Ser Pro Met Tyr Arg Leu Leu Tyr Asp Asp
                 85                  90                  95

Arg Asp Ile Phe Val Tyr Ser Asp Arg Glu Asn Met Arg Ala Glu Leu
                100                 105                 110

Gln Arg Val Phe Asp Glu Gly Thr Asp Gly Tyr Glu Gln Phe Met Glu
            115                 120                 125

Gln Glu Arg Lys Arg Phe Asn Ala Leu Tyr Pro Cys Ile Thr Arg Asp
130                 135                 140

Tyr Ser Ser Leu Lys Ser Phe Leu Ser Leu Asp Leu Ile Lys Ala Leu
145                 150                 155                 160

Pro Trp Leu Ala Phe Pro Lys Ser Val Phe Asn Asn Leu Gly Gln Tyr
                165                 170                 175

Phe Asn Gln Glu Lys Met Arg Leu Ala Phe Cys Phe Gln Ser Lys Tyr
            180                 185                 190

Leu Gly Met Ser Pro Trp Glu Cys Pro Ala Leu Phe Thr Met Leu Pro
        195                 200                 205

Tyr Leu Glu His Glu Tyr Gly Ile Tyr His Val Lys Gly Gly Leu Asn
210                 215                 220

Arg Ile Ala Ala Ala Met Ala Gln Val Ile Ala Glu Asn Gly Gly Glu
225                 230                 235                 240

Ile His Leu Asn Ser Glu Ile Glu Ser Leu Ile Ile Glu Asn Gly Ala
                245                 250                 255

Ala Lys Gly Val Lys Leu Gln His Gly Ala Glu Leu Arg Gly Asp Glu
            260                 265                 270

Val Ile Ile Asn Ala Asp Phe Ala His Ala Met Thr His Leu Val Lys
275                 280                 285

Pro Gly Val Leu Lys Lys Tyr Thr Pro Glu Asn Leu Lys Gln Arg Glu
        290                 295                 300

Tyr Ser Cys Ser Thr Phe Met Leu Tyr Leu Gly Leu Asp Lys Ile Tyr
305                 310                 315                 320

Asp Leu Pro His His Thr Ile Val Phe Ala Lys Asp Tyr Thr Thr Asn
                325                 330                 335

Ile Arg Asn Ile Phe Asp Asn Lys Thr Leu Thr Asp Phe Ser Phe
            340                 345                 350

Tyr Val Gln Asn Ala Ser Ala Ser Asp Asp Ser Leu Ala Pro Ala Gly
        355                 360                 365

Lys Ser Ala Leu Tyr Val Leu Val Pro Met Pro Asn Asn Asp Ser Gly
370                 375                 380

Leu Asp Trp Gln Ala His Cys Gln Asn Val Arg Glu Gln Val Leu Asp
```

```
            385                 390                 395                 400
        Thr Leu Gly Ala Arg Leu Gly Leu Ser Asp Ile Arg Ala His Ile Glu
                        405                 410                 415
        Cys Glu Lys Ile Ile Thr Pro Gln Thr Trp Glu Thr Asp His Val
                    420                 425                 430
        Tyr Lys Gly Ala Thr Phe Ser Leu Ser His Lys Phe Ser Gln Met Leu
                        435                 440                 445
        Tyr Trp Arg Pro His Asn Arg Phe Glu Leu Ala Asn Cys Tyr Leu
                450                 455                 460
        Val Gly Gly Thr His Pro Gly Ser Gly Leu Pro Thr Ile Tyr Glu
        465                 470                 475                 480
        Ser Ala Arg Ile Ser Ala Lys Leu Ile Ser Gln Lys His Arg Val Arg
                        485                 490                 495
        Phe Lys Asp Ile Ala His Ser Ala Trp Leu Lys Lys Ala Lys Ala
                    500                 505                 510

<210> SEQ ID NO 17
<211> LENGTH: 1491
<212> TYPE: DNA
<213> ORGANISM: Methylomonas 16a
<220> FEATURE:
<223> OTHER INFORMATION: ORF9

<400> SEQUENCE: 17
atgaactcaa atgacaacca acgcgtgatc gtgatcggcg ccggcctcgg cggcctgtcc      60
gccgctattt cgctggccac ggccggcttt tccgtgcaac tcatcgaaaa aaacgacaag     120
gtcggcggca agctcaacat catgaccaaa gacggcttta ccttcgatct ggggccgtcc     180
attttgacga tgccgcacat ctttgaggcc ttgttcacag gggccggcaa aaacatggcc     240
gattacgtgc aaatccagaa agtcgaaccg cactggcgca atttcttcga ggacggtagc     300
gtgatcgact tgtgcgaaga cgccgaaacc cagcgccgcg agctggataa acttggcccc     360
ggcacttacg cgcaattcca gcgctttctg gactattcga aaaacctctg cacggaaacc     420
gaagccggtt acttcgccaa gggcctggac ggcttttggg attactcaa gttttacggc     480 ccgctccgca gcctgctgag tttcgacgtc ttccgcagca tggaccaggg cgtgcgccgc     540
tttatttccg atcccaagtt ggtcgaaatc ctgaattact tcatcaaata cgtcggctcc     600
tcgccttacg atgcgcccgc cttgatgaac ctgctgcctt acattcaata tcattacggc     660
ctgtggtacg tgaaaggcgg catgtatggc atggcgcagg ccatggaaaa actggccgtg     720
gaattgggcg tcgagattcg tttagatgcc gaggtgtcgg aaatccaaaa acaggacggc     780
agagcctgcg ccgtaaagtt ggcgaacggc gacgtgctgc cggccgacat cgtggtgtcg     840
aacatggaag tgattccggc gatggaaaaa ctgctgcgca gcccggccag cgaactgaaa     900
aaaatgcagc gcttcgagcc tagctgttcc ggcctggtgc tgcacttggg cgtggacagg     960
ctgtatccgc aactggcgca ccacaatttc ttttattccg atcatccgcg cgaacatttc    1020
gatgcggtat tcaaaagcca tcgcctgtcg gacgatccga ccatttatct ggtcgcgccg    1080
tgcaagaccg accccgccca ggcgccggcc ggctgcgaga tcatcaaaat cctgccccat    1140
atcccgcacc tcgaccccga caaactgctg accgccgagg attattcagc cttgcgcgag    1200
cgggtgctgg tcaaactcga acgcatgggc ctgacggatt tacgccaaca catcgtgacc    1260
gaagaatact ggacgccgct ggatattcag gccaaatatt attcaaacca gggctcgatt    1320 tacgcgtgg tcgccgaccg cttcaaaaac ctgggtttca aggcacctca acgcagcagc    1380
```

```
gaattatcca atctgtattt cgtcggcggc agcgtcaatc ccggcggcgg catgccgatg      1440
gtgacgctgt ccgggcaatt ggtgagggac aagattgtgg cggatttgca a              1491
```

<210> SEQ ID NO 18
<211> LENGTH: 497
<212> TYPE: PRT
<213> ORGANISM: Methylomonas 16a
<220> FEATURE:
<223> OTHER INFORMATION: Amino acid sequences encoded by ORF9

<400> SEQUENCE: 18

```
Met Asn Ser Asn Asp Asn Gln Arg Val Ile Val Ile Gly Ala Gly Leu
 1               5                  10                  15

Gly Gly Leu Ser Ala Ala Ile Ser Leu Ala Thr Ala Gly Phe Ser Val
                20                  25                  30

Gln Leu Ile Glu Lys Asn Asp Lys Val Gly Gly Lys Leu Asn Ile Met
            35                  40                  45

Thr Lys Asp Gly Phe Thr Phe Asp Leu Gly Pro Ser Ile Leu Thr Met
        50                  55                  60

Pro His Ile Phe Glu Ala Leu Phe Thr Gly Ala Gly Lys Asn Met Ala
    65                  70                  75                  80

Asp Tyr Val Gln Ile Gln Lys Val Glu Pro His Trp Arg Asn Phe Phe
                85                  90                  95

Glu Asp Gly Ser Val Ile Asp Leu Cys Glu Asp Ala Glu Thr Gln Arg
               100                 105                 110

Arg Glu Leu Asp Lys Leu Gly Pro Gly Thr Tyr Ala Gln Phe Gln Arg
            115                 120                 125

Phe Leu Asp Tyr Ser Lys Asn Leu Cys Thr Glu Thr Glu Ala Gly Tyr
        130                 135                 140

Phe Ala Lys Gly Leu Asp Gly Phe Trp Asp Leu Leu Lys Phe Tyr Gly
    145                 150                 155                 160

Pro Leu Arg Ser Leu Leu Ser Phe Asp Val Phe Arg Ser Met Asp Gln
                165                 170                 175

Gly Val Arg Arg Phe Ile Ser Asp Pro Lys Leu Val Glu Ile Leu Asn
            180                 185                 190

Tyr Phe Ile Lys Tyr Val Gly Ser Ser Pro Tyr Asp Ala Pro Ala Leu
        195                 200                 205

Met Asn Leu Leu Pro Tyr Ile Gln Tyr His Tyr Gly Leu Trp Tyr Val
    210                 215                 220

Lys Gly Gly Met Tyr Gly Met Ala Gln Ala Met Glu Lys Leu Ala Val
225                 230                 235                 240

Glu Leu Gly Val Glu Ile Arg Leu Asp Ala Glu Val Ser Glu Ile Gln
                245                 250                 255

Lys Gln Asp Gly Arg Ala Cys Ala Val Lys Leu Ala Asn Gly Asp Val
            260                 265                 270

Leu Pro Ala Asp Ile Val Val Ser Asn Met Glu Val Ile Pro Ala Met
        275                 280                 285

Glu Lys Leu Leu Arg Ser Pro Ala Ser Glu Leu Lys Lys Met Gln Arg
    290                 295                 300

Phe Glu Pro Ser Cys Ser Gly Leu Val Leu His Leu Gly Val Asp Arg
305                 310                 315                 320

Leu Tyr Pro Gln Leu Ala His His Asn Phe Phe Tyr Ser Asp His Pro
                325                 330                 335

Arg Glu His Phe Asp Ala Val Phe Lys Ser His Arg Leu Ser Asp Asp
            340                 345                 350
```

-continued

```
Pro Thr Ile Tyr Leu Val Ala Pro Cys Lys Thr Asp Pro Ala Gln Ala
            355                 360                 365

Pro Ala Gly Cys Glu Ile Ile Lys Ile Leu Pro His Ile Pro His Leu
        370                 375                 380

Asp Pro Asp Lys Leu Leu Thr Ala Glu Asp Tyr Ser Ala Leu Arg Glu
385                 390                 395                 400

Arg Val Leu Val Lys Leu Glu Arg Met Gly Leu Thr Asp Leu Arg Gln
                405                 410                 415

His Ile Val Thr Glu Glu Tyr Trp Thr Pro Leu Asp Ile Gln Ala Lys
            420                 425                 430

Tyr Tyr Ser Asn Gln Gly Ser Ile Tyr Gly Val Val Ala Asp Arg Phe
        435                 440                 445

Lys Asn Leu Gly Phe Lys Ala Pro Gln Arg Ser Ser Glu Leu Ser Asn
    450                 455                 460

Leu Tyr Phe Val Gly Gly Ser Val Asn Pro Gly Gly Met Pro Met
465                 470                 475                 480

Val Thr Leu Ser Gly Gln Leu Val Arg Asp Lys Ile Val Ala Asp Leu
                485                 490                 495

Gln
```

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 19
aaggatccgc gtattcgtac tc                                        22

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 20
ctggatccga tctagaaata ggctcgagtt gtcgttcagg                      40

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 21
aaggatccta ctcgagctga catcagtgct                                30

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 22
gctctagatg caaccagaat cg                                        22

```
<210> SEQ ID NO 23
<211> LENGTH: 954
<212> TYPE: DNA
<213> ORGANISM: Methylomonas 16a

<400> SEQUENCE: 23
atgcaaatcg tactcgcaaa ccccgtgga ttctgtgccg gcgtggaccg ggccattgaa      60
attgtcgatc aagccatcga agcctttggt gcgccgattt atgtgcggca cgaggtggtg     120
cataaccgca ccgtggtcga tggactgaaa caaaaggtg cggtgttcat cgaggaacta     180
agcgatgtgc cggtgggttc ctacttgatt ttcagcgcgc acggcgtatc caaggaggtg     240
caacaggaag ccgaggagcg ccagttgacg gtattcgatg cgacttgtcc gctggtgacc     300
aaagtgcaca tgcaggttgc caagcatgcc aaacagggcc gagaagtgat tttgatcggc     360
cacgccggtc atccggaagt ggaaggcacg atgggccagt atgaaaaatg caccgaaggc     420
ggcggcattt atctggtcga aactccggaa gacgtacgca atttgaaagt caacaatccc     480
aatgatctgg cctatgtgac gcagacgacc ttgtcgatga ccgacaccaa ggtcatggtg     540
gatgcgttac gcgaacaatt tccgtccatt aaggagcaaa aaaaggacga tatttgttac     600
gcgacgcaaa accgtcagga tgcggtgcat gatctggcca agatttccga cctgattctg     660
gttgtcggct ctcccaatag ttcgaattcc aaccgtttgc gtgaaatcgc cgtgcaactc     720
ggtaaacccg cttatttgat cgatacttac caggatttga agcaagattg gctggaggga     780
attgaagtag tcggggttac cgcgggcgct tcggcgccgg aagtgttggt gcaggaagtg     840
atcgatcaac tgaaggcatg gggcggcgaa accacttcgg tcagagaaaa cagcggcatc     900
gaggaaaagg tagtcttttc gattcccaag gagttgaaaa acatatgca agcg           954

<210> SEQ ID NO 24
<211> LENGTH: 318
<212> TYPE: PRT
<213> ORGANISM: Methylomonas 16a

<400> SEQUENCE: 24

Met Gln Ile Val Leu Ala Asn Pro Arg Gly Phe Cys Ala Gly Val Asp
  1               5                  10                  15

Arg Ala Ile Glu Ile Val Asp Gln Ala Ile Glu Ala Phe Gly Ala Pro
             20                  25                  30

Ile Tyr Val Arg His Glu Val His Asn Arg Thr Val Val Asp Gly
         35                  40                  45

Leu Lys Gln Lys Gly Ala Val Phe Ile Glu Glu Leu Ser Asp Val Pro
     50                  55                  60

Val Gly Ser Tyr Leu Ile Phe Ser Ala His Gly Val Ser Lys Glu Val
 65                  70                  75                  80

Gln Gln Glu Ala Glu Glu Arg Gln Leu Thr Val Phe Asp Ala Thr Cys
                 85                  90                  95

Pro Leu Val Thr Lys Val His Met Gln Val Ala Lys His Ala Lys Gln
            100                 105                 110

Gly Arg Glu Val Ile Leu Ile Gly His Ala Gly His Pro Glu Val Glu
        115                 120                 125

Gly Thr Met Gly Gln Tyr Glu Lys Cys Thr Glu Gly Gly Ile Tyr
    130                 135                 140

Leu Val Glu Thr Pro Glu Asp Val Arg Asn Leu Lys Val Asn Asn Pro
145                 150                 155                 160

Asn Asp Leu Ala Tyr Val Thr Gln Thr Thr Leu Ser Met Thr Asp Thr
                165                 170                 175
```

-continued

```
Lys Val Met Val Asp Ala Leu Arg Glu Gln Phe Pro Ser Ile Lys Glu
            180                 185                 190

Gln Lys Lys Asp Asp Ile Cys Tyr Ala Thr Gln Asn Arg Gln Asp Ala
        195                 200                 205

Val His Asp Leu Ala Lys Ile Ser Asp Leu Ile Leu Val Val Gly Ser
    210                 215                 220

Pro Asn Ser Ser Asn Ser Asn Arg Leu Arg Glu Ile Ala Val Gln Leu
225                 230                 235                 240

Gly Lys Pro Ala Tyr Leu Ile Asp Thr Tyr Gln Asp Leu Lys Gln Asp
                245                 250                 255

Trp Leu Glu Gly Ile Glu Val Val Gly Val Thr Ala Gly Ala Ser Ala
            260                 265                 270

Pro Glu Val Leu Val Gln Glu Val Ile Asp Gln Leu Lys Ala Trp Gly
        275                 280                 285

Gly Glu Thr Thr Ser Val Arg Glu Asn Ser Gly Ile Glu Glu Lys Val
    290                 295                 300

Val Phe Ser Ile Pro Lys Glu Leu Lys Lys His Met Gln Ala
305                 310                 315
```